United States Patent
Lentz et al.

(10) Patent No.: US 11,090,228 B2
(45) Date of Patent: Aug. 17, 2021

(54) ADAPTER ASSEMBLY FOR ATTACHMENT TO A BOTTLE

(71) Applicant: BECTON DICKINSON AND COMPANY, Franklin Lakes, NJ (US)

(72) Inventors: Ammon David Lentz, York, PA (US); Brent D. Ludwig, Olathe, KS (US); Adam Steel, Fallston, MD (US); Ming-Hsiung Yeh, New Freedom, PA (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 16/325,617

(22) PCT Filed: Aug. 18, 2017

(86) PCT No.: PCT/US2017/047487
§ 371 (c)(1),
(2) Date: Feb. 14, 2019

(87) PCT Pub. No.: WO2018/035399
PCT Pub. Date: Feb. 22, 2018

(65) Prior Publication Data
US 2019/0183730 A1 Jun. 20, 2019

Related U.S. Application Data

(60) Provisional application No. 62/377,246, filed on Aug. 19, 2016.

(51) Int. Cl.
*A61J 1/20* (2006.01)
*G01N 33/49* (2006.01)
(Continued)

(52) U.S. Cl.
CPC .............. *A61J 1/2096* (2013.01); *A61J 7/00* (2013.01); *B65D 51/00* (2013.01); *G01N 1/2226* (2013.01);
(Continued)

(58) Field of Classification Search
CPC . A61J 1/2096; A61J 17/00; A61J 7/00; B65D 51/00; G01N 1/2226;
(Continued)

(56) References Cited

U.S. PATENT DOCUMENTS 2,541,272 A * 2/1951 Murphy .............. A61M 5/1782
141/285
3,608,550 A * 9/1971 Stawski ................ A61J 1/2096
604/414
(Continued)

FOREIGN PATENT DOCUMENTS

| CN | 101547674 A | 9/2009 |
| CN | 104470635 A | 3/2015 |

(Continued)

OTHER PUBLICATIONS

International Search Report from corresponding International Application No. PCT/US2017/047487 dated Nov. 6, 2017.
(Continued)

*Primary Examiner* — Timothy L Maust
*Assistant Examiner* — James R Hakomaki
(74) *Attorney, Agent, or Firm* — Botos Churchill IP Law LLP

(57) ABSTRACT

Various embodiments of the present disclosure describe systems and methods for testing samples (e.g., biological samples, environmental samples, food samples etc.) for microbial contamination. For example, some embodiments describe an adapter assembly with a means to penetrate a septum of a collection vessel and permit gaseous commu- (Continued)

nication between a headspace of the collection vessel and a sensor. In some embodiments, the gases in the headspace of the collection vessel can exit the collection vessel without contaminating the environment outside the system or allowing sample contamination. In some embodiments, the adapter assembly includes a membrane configured to prevent liquid in the collection vessel from contacting the sensor. In some embodiments, the adapter assembly can be used to access media inside the collection vessel for subculturing or aliquotting for another diagnostic process such as molecular diagnostics.

24 Claims, 17 Drawing Sheets

(51) Int. Cl.
G01N 1/22 (2006.01)
A61J 7/00 (2006.01)
B65D 51/00 (2006.01)
G01N 33/497 (2006.01)
A61M 5/32 (2006.01)

(52) U.S. Cl.
CPC .......... *G01N 33/4925* (2013.01); *A61M 5/32* (2013.01); *G01N 2001/2229* (2013.01); *G01N 2001/2241* (2013.01); *G01N 2033/4977* (2013.01)

(58) Field of Classification Search
CPC ....... G01N 33/4925; G01N 2001/2229; G01N 2001/2241; G01N 2033/4977; G01N 33/4825; A61M 5/32
USPC ................. 141/330; 435/287.5; 604/411, 86
See application file for complete search history.

(56) References Cited

U.S. PATENT DOCUMENTS

| | | | | |
|---|---|---|---|---|
| 4,058,121 A * | 11/1977 | Choksi | ................. | A61J 1/2096 604/411 |
| 4,073,691 A * | 2/1978 | Ahnell | ................. | C12Q 1/04 435/34 |
| 4,220,715 A * | 9/1980 | Ahnell | ................. | C12Q 1/04 435/287.1 |
| 4,543,101 A * | 9/1985 | Crouch | ................. | A61J 1/2096 604/411 |
| 4,768,568 A * | 9/1988 | Fournier | ............... | A61J 1/2089 141/27 |
| 4,834,149 A * | 5/1989 | Fournier | ............... | A61J 1/2089 141/1 |
| 4,894,052 A * | 1/1990 | Crawford | .......... | A61M 25/0693 604/507 |
| 4,935,020 A * | 6/1990 | Broden | ................ | G01N 33/491 604/411 |
| 5,042,690 A * | 8/1991 | O'Meara | ............. | B65D 51/222 222/83 |
| 5,046,496 A * | 9/1991 | Betts | .................. | G01N 33/4925 600/352 |
| 5,155,019 A * | 10/1992 | Sussman | ................ | C12M 41/34 250/343 |
| 5,169,602 A * | 12/1992 | Pang | ........................ | A61J 1/20 215/247 |
| 5,211,638 A * | 5/1993 | Dudar | .................. | A61J 1/2089 604/411 |
| 5,232,839 A * | 8/1993 | Eden | ...................... | C12M 41/46 435/287.4 |
| 5,701,910 A * | 12/1997 | Powles | .............. | A61B 10/0283 600/577 |
| 5,769,552 A * | 6/1998 | Kelley | .................... | B65D 47/38 222/83 |
| 5,770,153 A * | 6/1998 | Wagner | .................... | G01N 7/00 422/79 |
| 5,807,701 A * | 9/1998 | Payne | ...................... | C12Q 1/04 422/50 |
| 5,856,175 A * | 1/1999 | Thorpe | .................. | C12M 41/26 422/82.13 |
| 5,891,739 A * | 4/1999 | Berndt | .................. | C12M 41/46 436/518 |
| 6,170,318 B1 * | 1/2001 | Lewis | .................. | G01N 27/126 340/632 |
| 6,190,858 B1 * | 2/2001 | Persaud | .................. | C12Q 1/04 435/283.1 |
| 6,368,558 B1 | 4/2002 | Suslick et al. | | |
| 6,378,714 B1 * | 4/2002 | Jansen | .................. | A61J 1/1406 141/329 |
| 6,601,721 B2 * | 8/2003 | Jansen | .................. | A61J 1/1406 141/329 |
| 6,903,823 B1 | 6/2005 | Mueller et al. | | |
| 7,112,416 B2 * | 9/2006 | Sullivan | .................. | C12Q 1/04 435/34 |
| 7,261,857 B2 | 8/2007 | Suslick et al. | | |
| 7,799,009 B2 * | 9/2010 | Niedospial, Jr. | ....... | A61J 1/2096 604/411 |
| 8,167,863 B2 | 5/2012 | Yow | | |
| 8,388,905 B2 * | 3/2013 | Neel | ................ | G01N 33/48757 422/401 |
| 8,802,034 B2 * | 8/2014 | Bartfeld | .................. | B01L 3/502 422/536 |
| 8,852,504 B2 | 10/2014 | Suslick et al. | | |
| 9,067,014 B2 * | 6/2015 | Nelson | .................. | A61M 5/168 |
| 9,095,292 B2 * | 8/2015 | Zanzucchi | ............. | A61B 5/157 |
| 9,249,446 B2 | 2/2016 | Suslick et al. | | |
| 9,468,404 B2 * | 10/2016 | Hayden | ........... | A61B 5/150923 |
| 9,605,294 B2 * | 3/2017 | Berndt | .................... | C12Q 1/24 |
| 9,856,446 B2 * | 1/2018 | Suslick | .................... | C12Q 1/10 |
| 10,139,322 B2 | 11/2018 | Olivier et al. | | |
| 2006/0223052 A1 * | 10/2006 | MacDonald | ............. | C12Q 1/04 435/5 |
| 2007/0078313 A1 * | 4/2007 | Emery | ............. | A61B 5/150022 600/316 |
| 2008/0015496 A1 * | 1/2008 | Hamedi-Sangsari | ....... | A61J 1/2089 604/87 |
| 2010/0036319 A1 * | 2/2010 | Drake | .................... | A61J 1/1406 604/135 |
| 2010/0166604 A1 | 7/2010 | Lim et al. | | |
| 2012/0150128 A1 * | 6/2012 | Zhao | .................... | A61M 5/3293 604/239 |
| 2015/0013837 A1 * | 1/2015 | Barrelle | ................. | A61J 1/2082 141/89 |
| 2015/0087015 A1 * | 3/2015 | Bos | .................... | B01L 3/50825 435/34 |
| 2015/0099694 A1 * | 4/2015 | Lim | ......................... | C12Q 1/04 514/2.7 |
| 2015/0238909 A1 * | 8/2015 | Mori | ......................... | B32B 5/16 96/12 |
| 2017/0078396 A1 * | 3/2017 | Haas | ...................... | G16H 40/63 |
| 2019/0183730 A1 | 6/2019 | Lentz et al. | | |

FOREIGN PATENT DOCUMENTS

CN 207845648 U 9/2018
WO 2013/165243 A1 11/2013

OTHER PUBLICATIONS

Lim, Sung H., et al., "Colorimetric Sensor Array Allows Fast Detection and Simultaneous Identification of Sepsis-Causing Bacteria in Spiked Blood Culture", J. Clin. Micro. vol. 52 (2), Feb. 2014, 592-598.
"Chinese Office Action issued in corresponding Chinese Application No. 201780050460.7 dated Feb. 3, 2020."
Chinese Second Office Action issued in CN application No. 2017800504607 dated Sep. 29, 2020.

(56) References Cited

OTHER PUBLICATIONS

Third Chinese Office Action issued in corresponding CN application No. 2017800504607 dated Mar. 18, 2021, 7 pages.

* cited by examiner

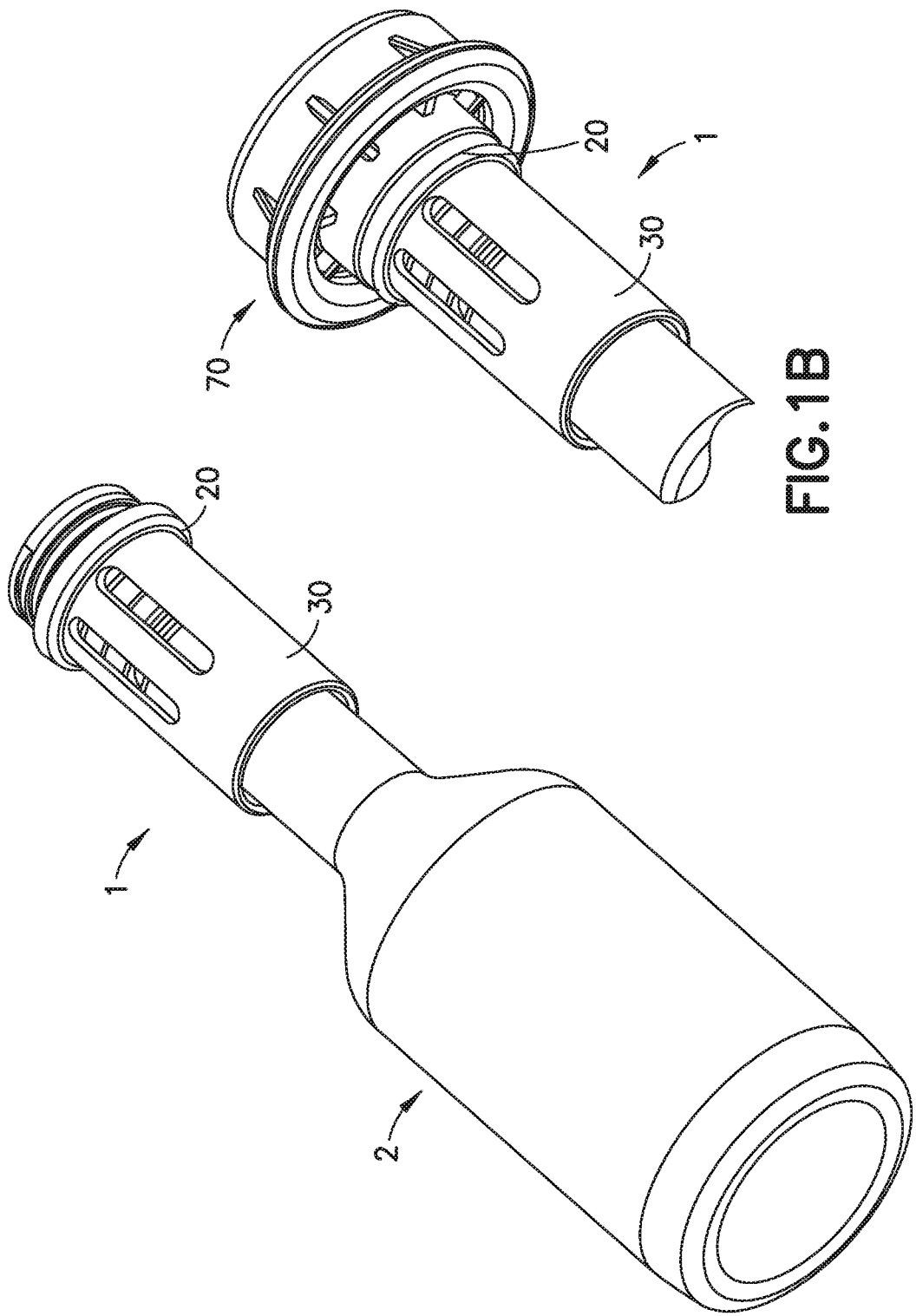

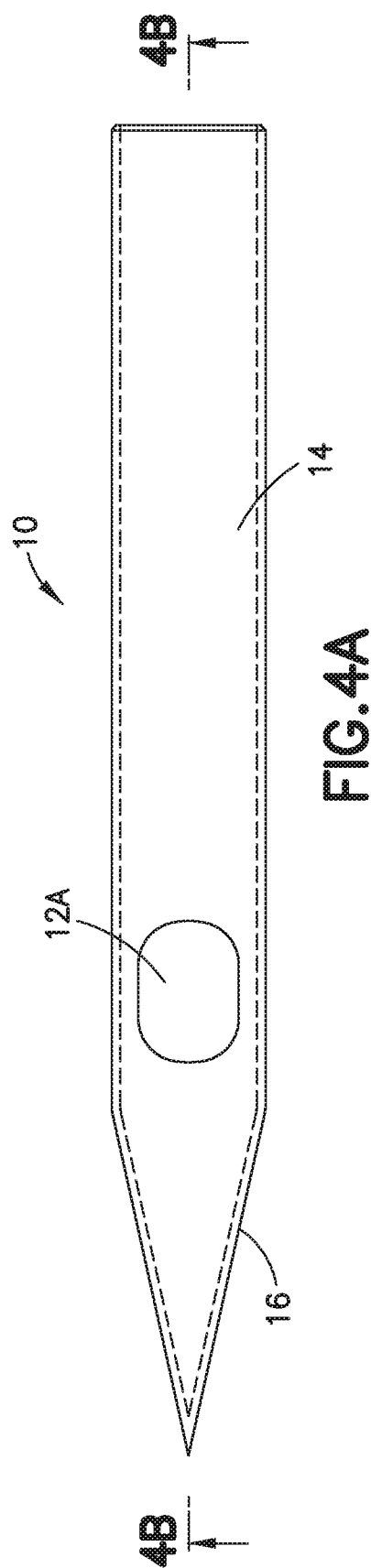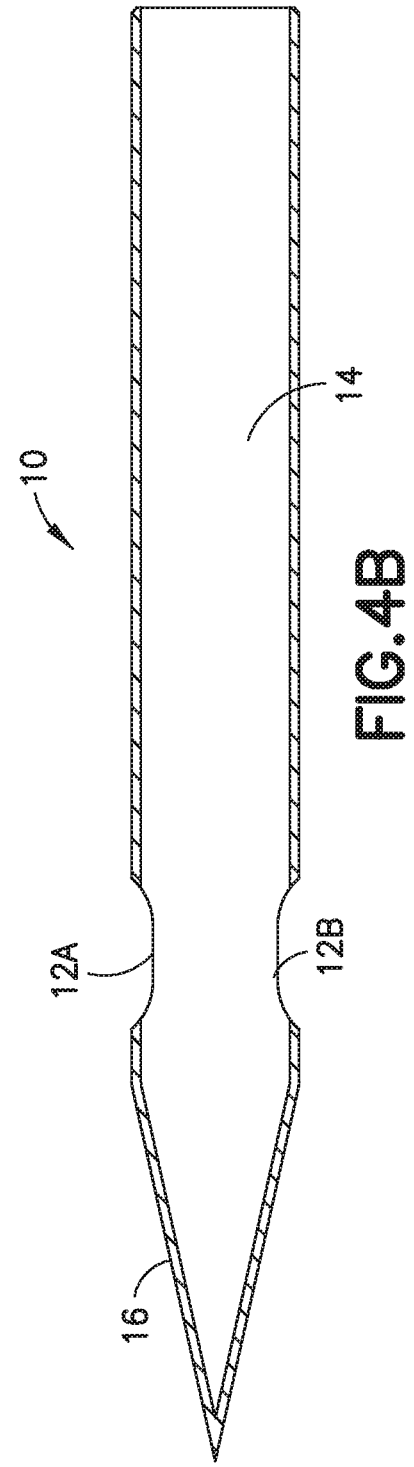

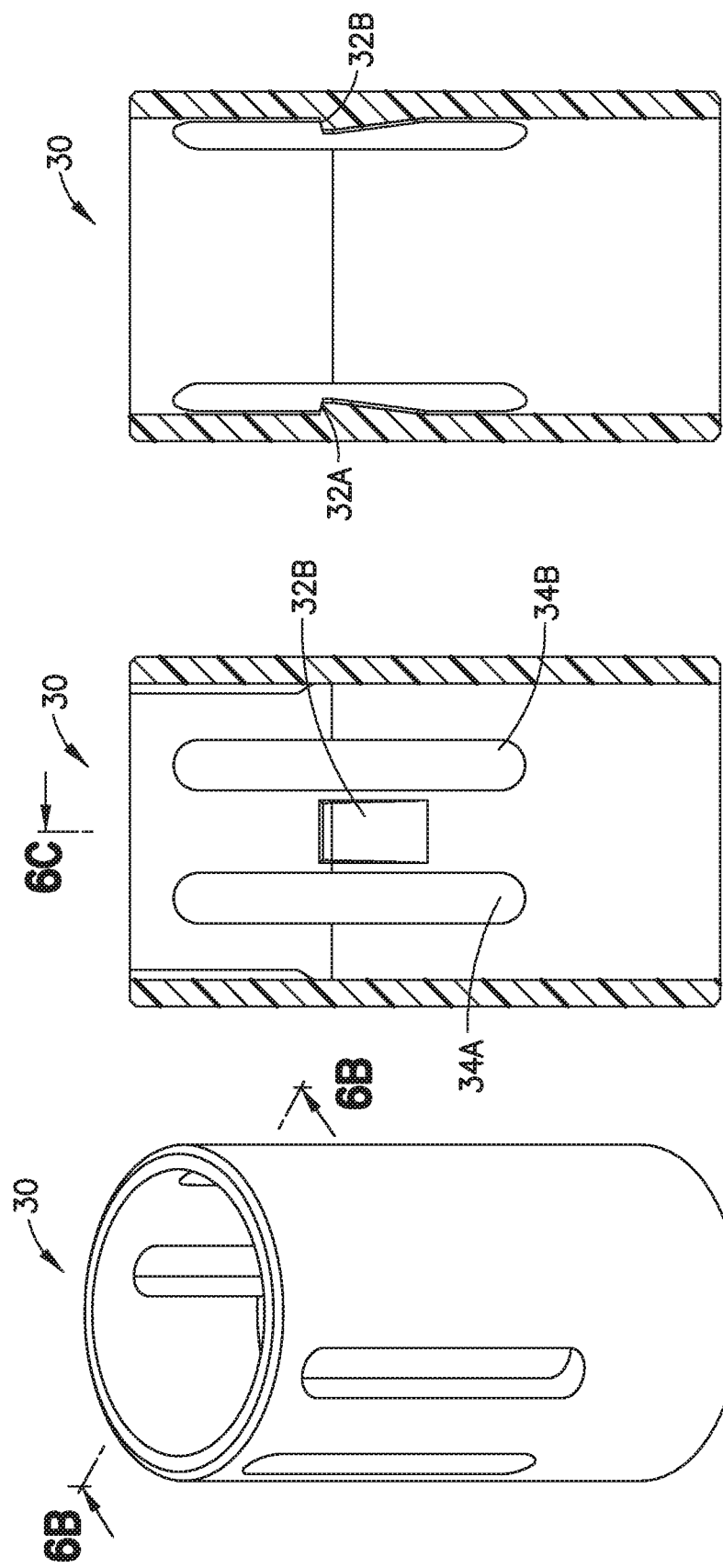

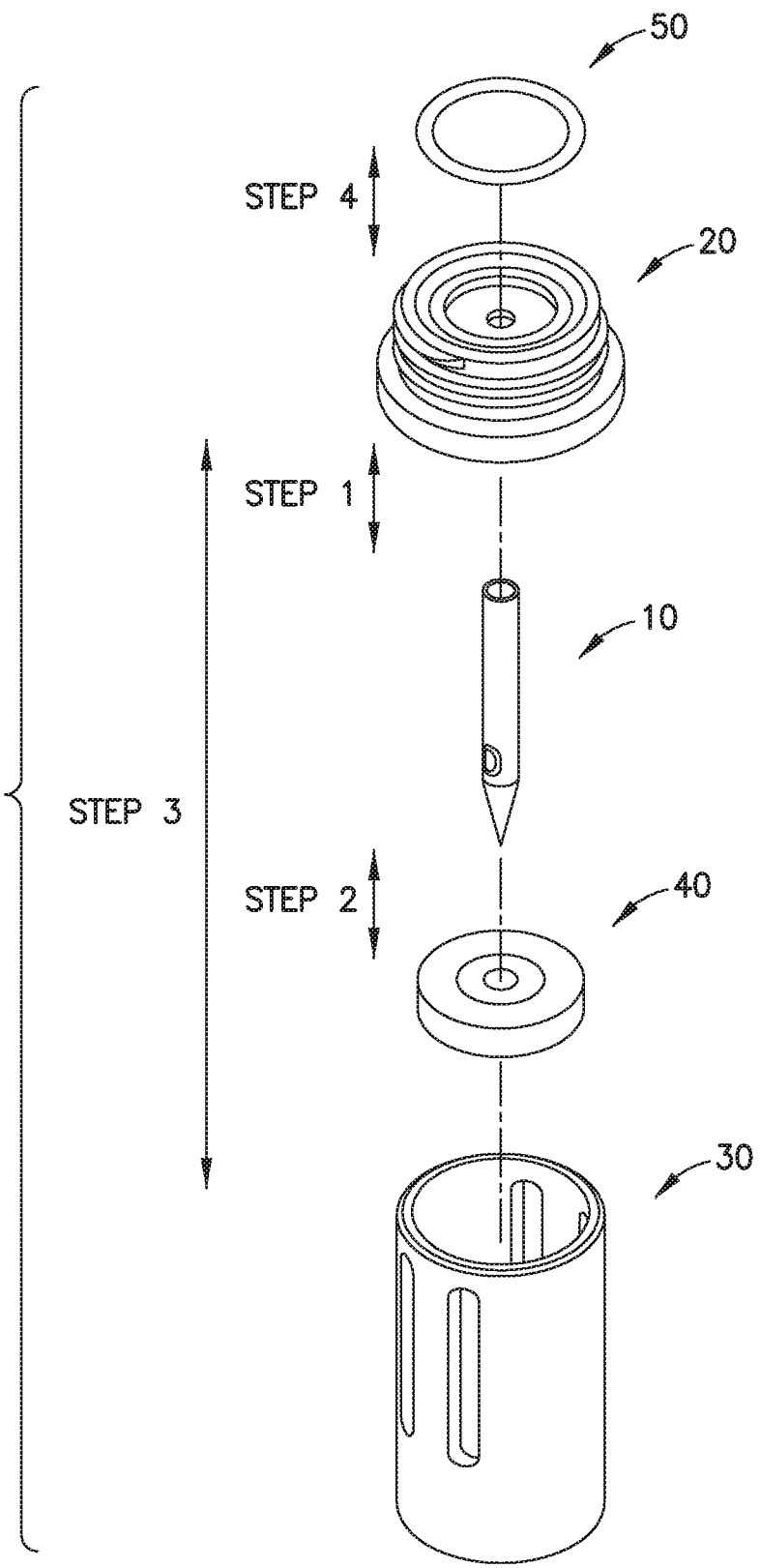

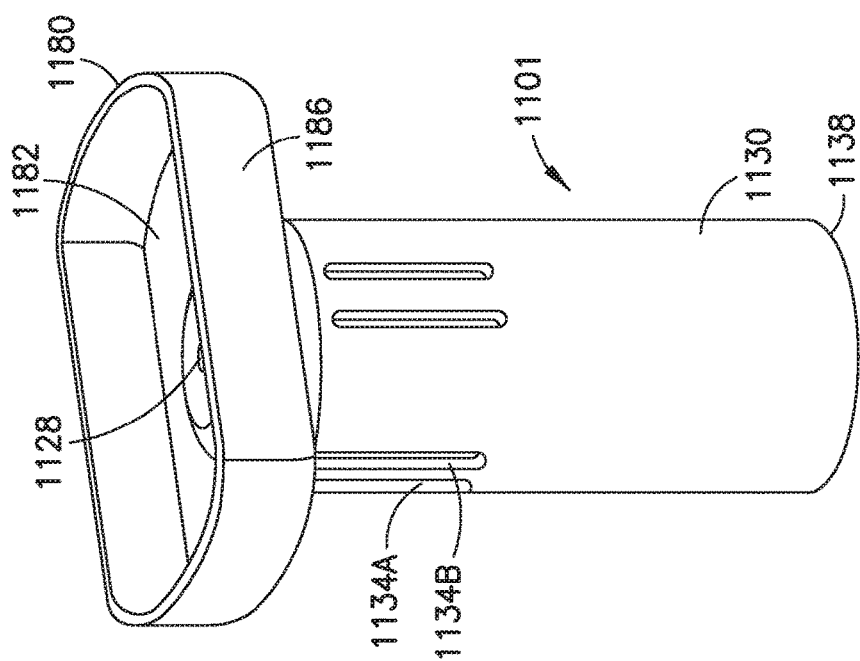
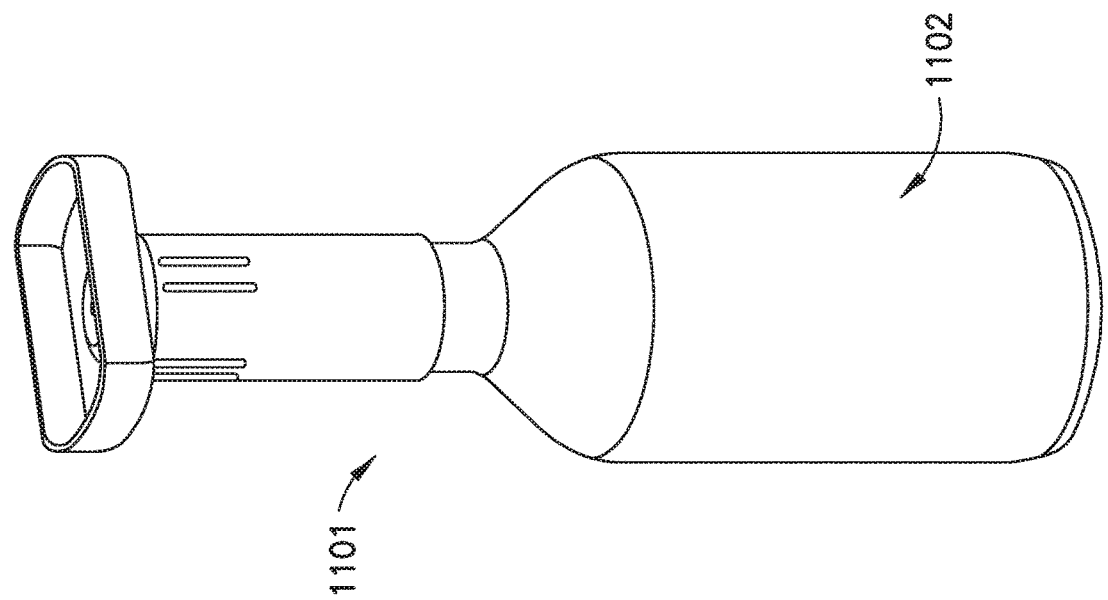

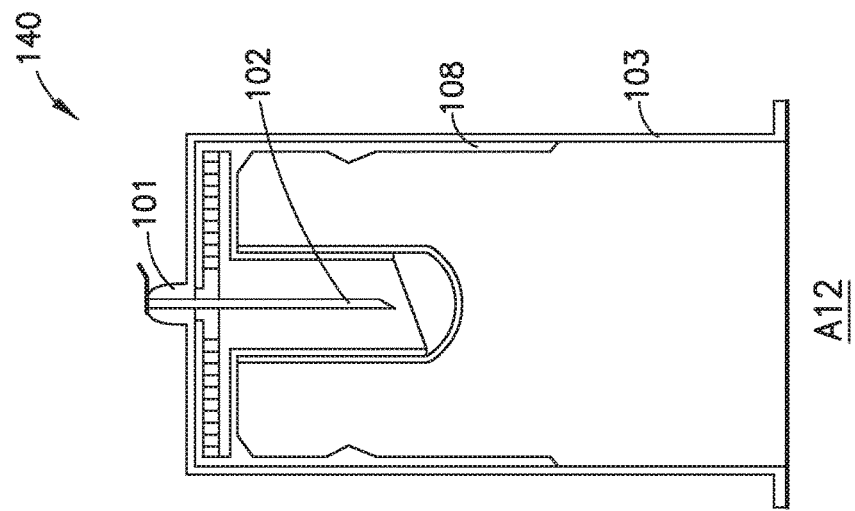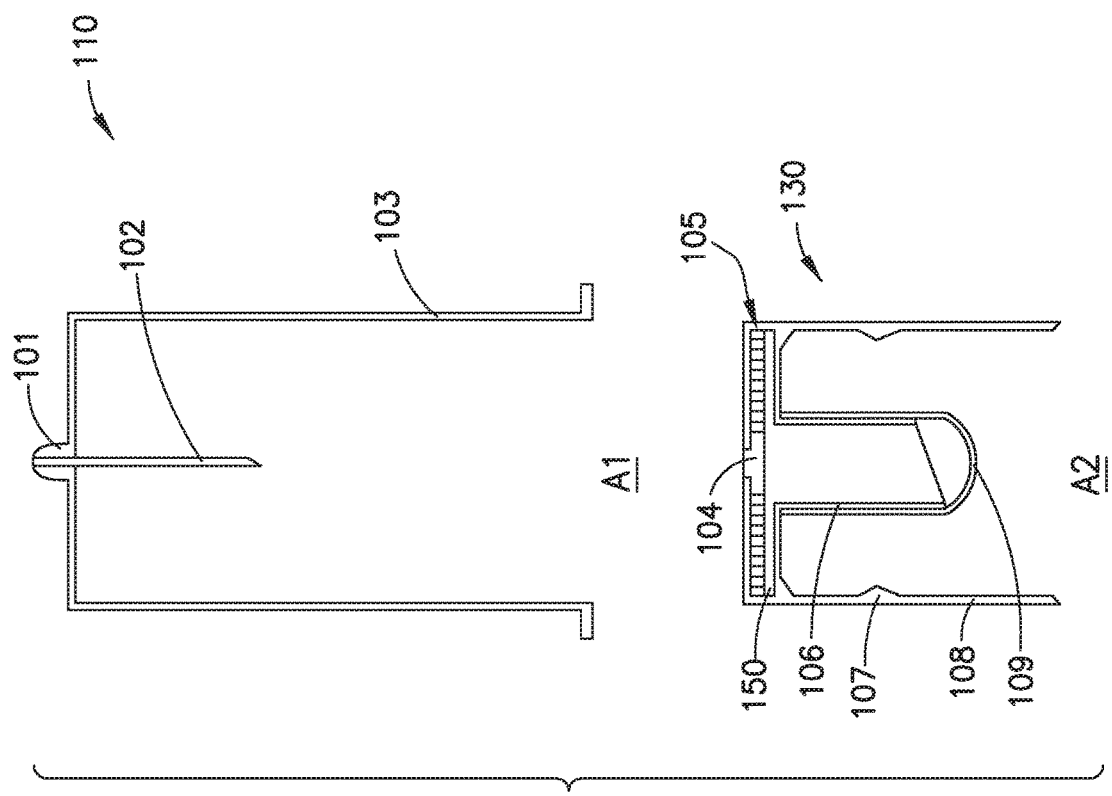

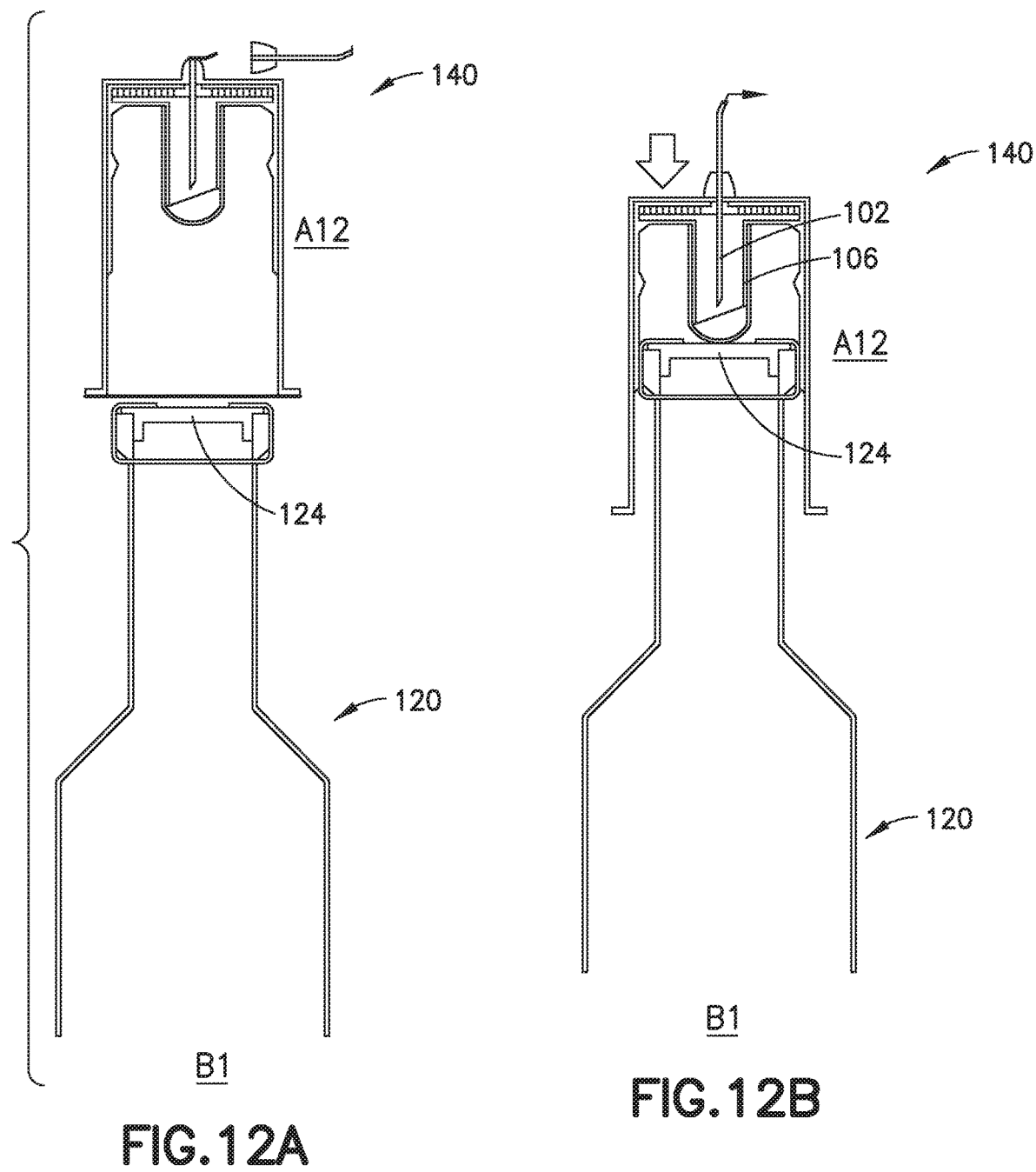

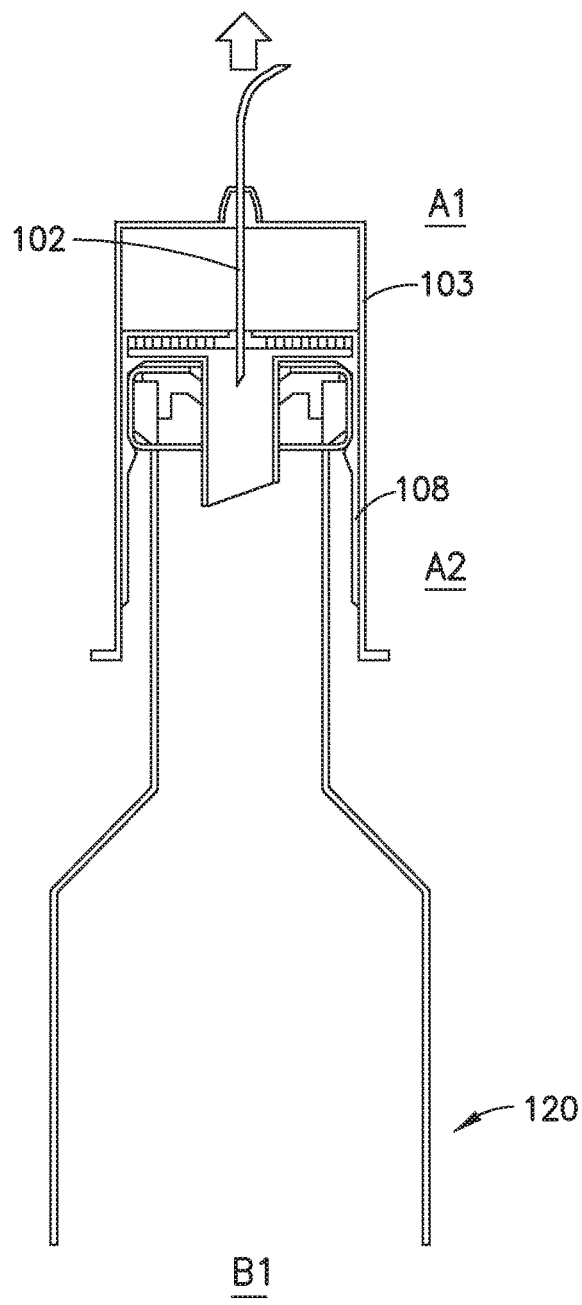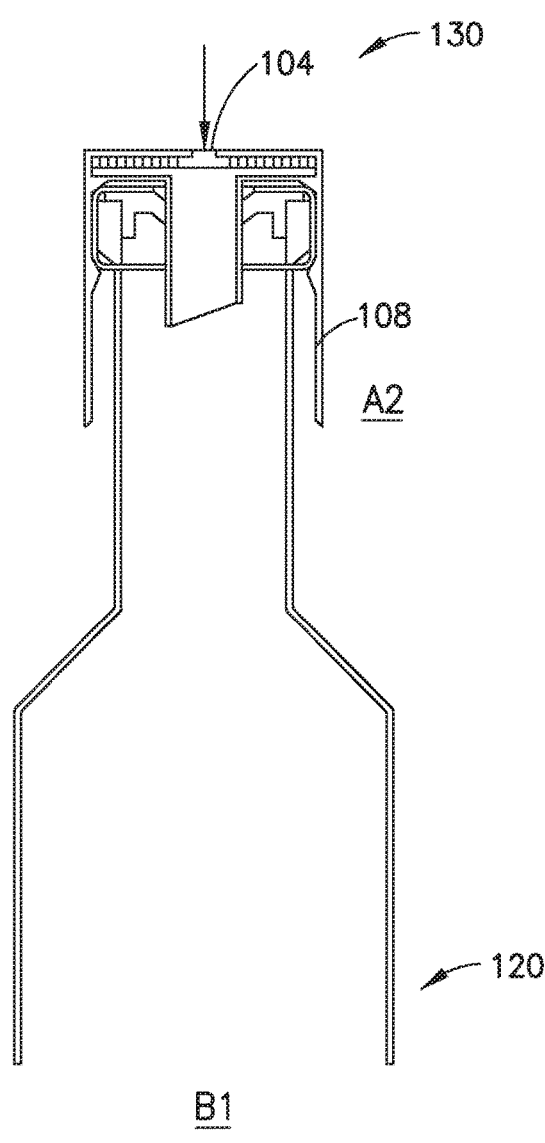
FIG.12E
FIG.12F

ADAPTER ASSEMBLY FOR ATTACHMENT TO A BOTTLE

CROSS-REFERENCE TO RELATED APPLICATIONS

The present application is a national phase entry under 35 U.S.C. § 371 of International Application No. PCT/US2017/047487, filed Aug. 18, 2017, published in English, which claims priority from U.S. Provisional Application No. 62/377,246, filed Aug. 19, 2016, the disclosures of which are incorporated herein by reference.

TECHNICAL FIELD

Various embodiments of the present disclosure describe systems and methods for testing samples (e.g., biological samples, environmental samples, food samples etc.) for microbial contamination. For example, some embodiments describe an adapter assembly with a means to penetrate a septum of a collection vessel and permit gaseous communication between a headspace of the collection vessel and a sensor.

BACKGROUND

Sepsis is a significant healthcare issue due to its high frequency of occurrence and high mortality rate in hospitals. Sepsis is characterized by a whole-body inflammatory state, referred a systemic inflammatory response ("SIRS"), and by the presence of a known or suspected infection. The immune system may cause this inflammatory response as a consequence of microbes in, for example, the blood, urine, lungs, skin, or other tissues. One of the leading causes of sepsis is a bloodstream infection ("BSI"). BSI is most commonly diagnosed by a blood culture in which a sample of blood is incubated with a medium in an atmosphere controlled to promote bacterial growth.

Sensor array methods for rapid detection and identification of microorganisms in biological samples (e.g., blood samples) have been described. See, e.g., U.S. Pat. Nos. 9,249,446, 8,852,504, 7,261,857, 6,368,558, U.S. Publication No. 2010/0166604, and Sung, H., et al., "Colorimetric Sensor Array Allows Fast Detection and Simultaneous Identification of Sepsis-Causing Bacteria in Spiked Blood Culture," J. Clin. Microbiol., Vol. 52(2), pp. 592-598 (February 2014).

BRIEF SUMMARY

Various embodiments of the present disclosure describe systems and methods for testing samples (e.g., biological samples, environmental samples, food samples etc.) for microbial contamination. For example, some embodiments describe an adapter assembly with a means to penetrate a septum of a collection vessel and permit gaseous communication between a headspace of the collection vessel and a sensor. In some embodiments, the gases in the headspace of the collection vessel can exit the collection vessel without contaminating the environment outside the system or allowing sample contamination. In some embodiments, the adapter assembly includes a gas permeable membrane configured to prevent liquid in the collection vessel from contacting the sensor. In some embodiments, the adapter assembly can be used to access media inside the collection vessel for subculturing or aliquotting for another diagnostic process such as molecular diagnostics.

One aspect of the present disclosure relates to an adapter assembly comprising: a sleeve configured to engage a collection vessel; a cannula configured to penetrate a septum of the collection vessel; and a sensor assembly interface configured to engage a sensor assembly with a sensor capable of detecting changes in a composition of the gases in a headspace of the collection vessel, wherein the sensor assembly interface is connected to the sleeve and the cannula, wherein the adapter assembly is configured such that when (i) the sleeve is engaged with a collection vessel and (ii) the sensor assembly interface is engaged with a sensor assembly: (a) the sensor assembly interface and the cannula provide a flow pathway for delivering gases from the headspace of the collection vessel to the sensor of the sensor assembly; and (b) the sensor assembly interface defines at least a portion of a chamber for collecting the gases in the flow pathway from the headspace of the collection vessel.

In some embodiments, the adapter assembly is configured to form a closed system when (i) the sleeve is engaged with a collection vessel and (ii) the sensor assembly interface is engaged with a sensor assembly.

In some embodiments, the sensor assembly interface includes a membrane configured to: allow gases in the flow pathway to flow toward the sensor; and prevent liquid in the collection vessel from contacting the sensor. In some embodiments, the membrane is interposed between the portion of the sensor assembly interface and the portion of the sensor assembly. In some embodiments, the membrane is a polytetrafluoroethylene (e.g. TEFLON) material embedded with a stainless steel mesh.

In some embodiments, the sleeve includes two opposing latches for engaging the collection vessel, wherein both latches taper inward from a wall of the sleeve in a proximal direction towards a top rim of the sleeve. In some embodiments, the sleeve includes two pairs of stress relief slots extending longitudinally on opposite sides of the body, and wherein one of the two opposing latches is positioned between one of the two pairs of stress relief slots, and wherein the other opposing latch is position between the other pair of stress relief slots.

In some embodiments, the cannula includes a first portion that is substantially cylindrical and a second portion that is tapered to a point at one end, and wherein the first portion includes at least one port. In some embodiments, the cannula comprises two ports located approximately opposite each other on the cannula.

In some embodiments, the sensor assembly interface is an adapter ring having a substantially cylindrical shape. In some embodiments, the adapter ring has a plurality of circumferentially distributed threads for engaging the sensor assembly. In some embodiments, the sleeve includes a substantially cylindrical body, the adapter ring seals one end of the body of the sleeve, and the cannula is disposed in a central opening of the adapter ring and extends therethrough. In some embodiments, a circular spacer is disposed on a bottom surface of the adapter ring around the cannula; and an o-ring is disposed on a top surface of the adapter ring, wherein the o-ring forms a gas tight seal when the sensor assembly interface is engaged with the sensor assembly.

In some embodiments, the sleeve and the sensor assembly interface are monolithically integrated as a single component. In some embodiments, the sleeve and the sensor assembly interface are separate components attached together.

In some embodiments, the adapter assembly includes the sensor assembly, wherein (i) the sensor assembly is welded to the sensor assembly interface, (ii) attached to the sensor assembly interface with an adhesive, or (iii) the sensor assembly and the sensor assembly interface are monolithically integrated as a single component.

In some embodiments, the adapter assembly includes the sensor assembly and a septum disposed on a top surface of the sensor assembly such that a needle having a smaller diameter than the cannula can puncture the septum disposed on the top of the sensor assembly and enter the collection vessel through the cannula and the chamber. In some embodiments, the adapter assembly includes a first housing comprising the sleeve, the cannula, the sensor assembly interface, and the sensor assembly; and a second housing comprising a needle having a smaller diameter than the cannula, wherein the first housing is loosely fitted inside the second housing. In some embodiments, the second housing is a holder for blood collection. In some embodiments, the cannula pierces a seal on a container as the first housing is advance onto the container. In some embodiments, the needle has a channel that is in fluid communication with the collection vessel when the first and second housings are assembled and fitted onto the collection vessel.

BRIEF DESCRIPTION OF DRAWINGS

FIG. 1A is an external profile view of an adapter assembly in one embodiment of the invention secured onto a bottle.

FIG. 1B is a close up partial profile view of the adapter assembly of FIG. 1A shown with a sensor attached.

FIG. 4A is a side view of a cannula included as part of the adapter assembly.

FIG. 4B is a sectional view of the cannula shown in FIG. 4A.

FIG. 6A is a profile view of the sleeve of the adapter assembly.

FIG. 6B is a section view of the sleeve shown in FIG. 6A.

FIG. 6C is another section view of the sleeve shown in FIG. 6A.

FIG. 7 illustrates a sequence of assembly for several components of the adapter assembly.

FIG. 8A is a profile view of another embodiment of an adapter assembly shown secured onto a bottle.

FIG. 8B is a profile view of the adapter assembly shown in FIG. 8A.

FIGS. 11A and 11B are schematic views illustrating the operation of an alternative adaptor for a sensor array that will be secured to a sample collection container.

FIGS. 12A through 12F illustrate the collection of sample into a container with a sensor array disposed thereon.

DETAILED DESCRIPTION

Figure 2A:
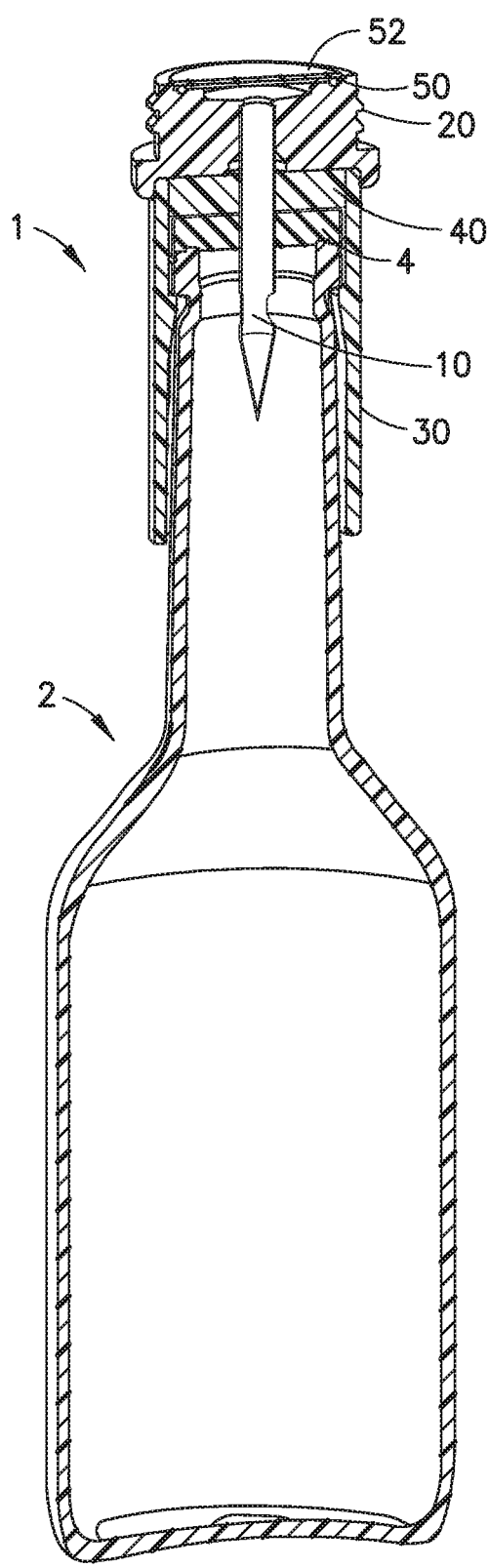
FIG. 2A is a sectional view of the adapter assembly secured onto a bottle.

Embodiments of the present disclosure are described in detail with reference to the drawing figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Disclosed herein are systems and methods for testing samples (e.g., biological samples, environmental samples, food samples etc.) for microbial contamination. Such systems require an environment in which the sample is evaluated with a high certainty that the sample has not been contaminated after collection, which could lead to a false positive. As such, the systems and methods contemplate introducing the collected sample into a sterile collection vessel that is sealed and remains sealed from the environment (e.g., one of Becton, Dickinson and Company's ("BD's") BACTEC™ bottles). The sample is then subjected to conditions that will support microbial growth if microbes are present in the sample. Such conditions include nutrient media to support microbial growth and incubation conditions that support microbial growth. For example, in some embodiments, the collection vessel may contain a BD blood culture media, such as BD's BACTEC™ Peds Plus™ medium, BD's BACTEC™ Plus Aerobic medium, BD's BACTEC™ Plus Anaerobic medium, BD's BACTEC™ Lytic Anaerobic medium, BD's BACTEC™ Standard Aerobic medium, or BD's BACTEC™ Standard Anaerobic medium. One exemplary system for evaluating samples for microbial growth is BD's BACTEC™ system.

Described herein are systems and methods for evaluating samples for microbial contamination by providing a system that includes a collection vessel that can receive a sample for testing with a very low probability of sample contamination. The collection vessel contains a nutrient media. When the sample is incubated in the nutrient media, microorganisms, if present, will begin to grow. The metabolic processes of microbial growth will generate carbon dioxide or oxygen (depending on the organism). An increase in oxygen or carbon dioxide indicates that the sample contains microbes. To make this determination, the sample is in gaseous communication with a sensor that can detect changes in the composition of the gas headspace of the system. Such gaseous communication should be in a sealed environment (e.g., a closed system) that prevents ingassing or outgassing, to ensure that the sample is not contaminated from the environment outside the system and to ensure that the environment outside the system is not contaminated by the contents of the system.

In such systems, the sample is first collected into a sterile collection vessel. After collection, an adapter assembly may be secured on to the collection vessel. The adapter assembly can penetrate a septum of the collection vessel and provide a flow pathway for delivering gases from the headspace of the collection vessel to the sensor while the system retains a gas tight seal. Although reference is made to particular sensors throughout the disclosure, assemblies for other sensor types can also be secured to a collection vessel with an adapter assembly of the present invention. For example, another sensor type with an assembly securable with adapter assembly includes a cuvette for optical analysis of gases. More broadly, it is contemplated that the adapter assembly described herein can be used for purposes other than those relating to a sensor as described above. For example, the adapter assembly can be used to access media inside a bottle for subculturing or aliquotting for another diagnostic process such as molecular diagnostics. For applications in which access to the bottle interior are required, barriers to such access (e.g., liquid barrier membranes) might have to be modified or eliminated.

A first aspect of the invention relates to an adapter assembly configured to be secured to a collection vessel so that gases from the collection vessel can exit the collection vessel without contaminating the environment outside the system or allowing sample contamination. In one embodiment, the adapter assembly includes a cannula, an adapter ring, a sleeve, a spacer and an o-ring. One end of the cannula is disposed in an opening in the centerline adapter ring. A spacer is positioned over the cannula so that it is adjacent to a bottom surface of the adapter ring. A second end of the cannula includes at least two ports and is positioned so that spacer separates the second end from the first end. The o-ring is disposed on a top surface of the adapter ring. Collectively, the adapter ring, o-ring, cannula and spacer may be disposed on the sleeve. The top surface of the adapter ring defines a recess so that when another element, such as a membrane, is placed over the adapter ring, a chamber is formed that defines the extent of the gas interface of the bottle headspace with the membrane. The two ports of the cannula each have a thickness measured parallel to a length of the cannula that is less than a thickness of a septum of the bottle and a combined surface area greater than an inner diameter of the cannula. The sleeve includes surface features to engage with the bottle so that, even under pressure, the adapter assembly remains engaged with and retained on the bottle. The sleeve material may be a polymer with mechanical properties that allow elastic deformation of the surface features (e.g., latches, etc.). Suitable polymers include but are not limited to polycarbonate, PC/ABS alloy, or any plastic with similar mechanical properties.

One example of an adapter assembly is illustrated in FIGS. 1A-6C. More specifically, FIGS. 1A-3 provide various perspectives of how adapter assembly 1 may be attached to bottle 2, FIGS. 1B and 2B illustrate how sensor assembly 70 may be attached to adapter assembly 1, and FIGS. 4A-6C illustrate certain components of adapter assembly 1 in greater detail. As shown in these illustrations, adapter assembly 1 includes cannula 10, adapter ring 20, sleeve 30, spacer 40, o-ring 50, and membrane 52. Cannula 10 is disposed in the longitudinal center (e.g., within cylindrical passage 28) of adapter ring 20. An adhesive (not shown), such as a UV cured epoxy, may be used to hold cannula 10 in place. Adapter ring 20 is disposed around an outer perimeter of sleeve 30. Spacer 40 is disposed on a bottom surface of adapter ring 20 and positioned within sleeve 30. O-ring 50 and membrane 52 are disposed on the top surface of adapter ring 20. When positioned over bottle 2, sleeve 30 of adapter assembly 1 is disposed adjacent to an outer surface of bottle 2 and cannula 10 penetrates septum 4 of bottle 2. The individual components of adapter assembly 1 and sensor assembly 70 are described in more detail below. In alternative embodiments, the adapter assembly 1 includes the sensor assembly 70, wherein (i) the sensor assembly 70 is welded to the adapter ring 20, (ii) attached to the adapter ring with an adhesive, or (iii) the sensor assembly 70 and the adapter ring are monolithically integrated as a single component.

As best shown in FIGS. 4A and 4B, cannula 10 includes a first portion 14 that is substantially cylindrical and a second portion 16 that is tapered to a point at one end. Ports 12A and 12B are positioned on opposite facing surfaces of the first portion 14 of cannula 10. As best shown in FIG. 3, in one embodiment, a combined area of ports 12A and 12B is greater than a cross-sectional area of cannula 10, and a depth of each port measured parallel to a longitudinal axis of cannula 10 is less than the thickness of septum 4 on bottle 2. This ensures that the ports are disposed entirely below the septum 4, when the adapter is placed on and secured onto the bottle 2, but never even partially disposed in the bottle headspace 6 until the adapter forms a seal on the bottle. As shown in FIGS. 1A-6C, cannula 10 is BD's Whiteacre point cannula. Advantageously ports 12A and 12B of cannula 10 help ensure that a clear channel is maintained between bottle 2 and sensor assembly 70 when the adapter assembly 1 is secured to bottle 2 and sensor assembly 70. By using two or more ports, the risk of any blockage of gases or fluids in cannula 10 is greatly reduced.

As shown in FIGS. 1A-6C, adapter ring 20 is generally cylindrical in shape. Moreover, an outer surface of adapter ring 20 includes threads 22, which are distributed circumferentially around ring 20. Threads 22 allow sensor assembly 70 to be threaded onto adapter ring 20. However a sensor assembly can be secured to an adapter ring by any conventional means. As shown in FIGS. 1A-6C, adapter ring 20 also includes connection extension 26, which is sized and positioned to fit over and engage sleeve 30. As best shown in FIGS. 1A and 1B, connection extension 26 forms an annular ring around adapter ring 20. FIGS. 1A-3 illustrate the appearance of adapter ring 20 as positioned over and secured with sleeve 30. Adapter ring 20 may be constructed with a clear polycarbonate. This material advantageously allows UV light to penetrate through adapter ring 20 and reach a mating surface between adapter ring 20 and cannula 10. With a UV cured adhesive joining adapter ring 20 and cannula 10 as described above, the penetrating UV light can cure the adhesive to form a bond between the two elements.

Figure 5A:
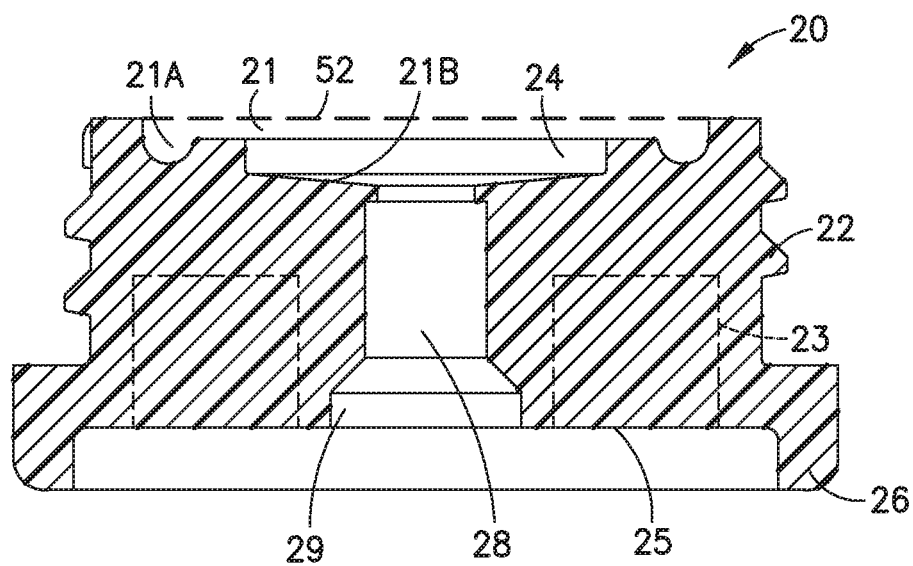
FIG. 5A is a sectional view of an adapter ring included as part of the adapter assembly.
Figure 5B:
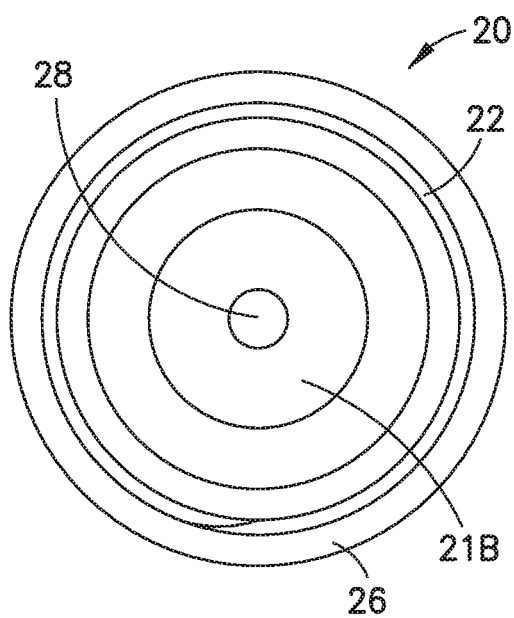
FIG. 5B is a top view of the adapter ring shown in FIG. 5A.
Figure 5C:
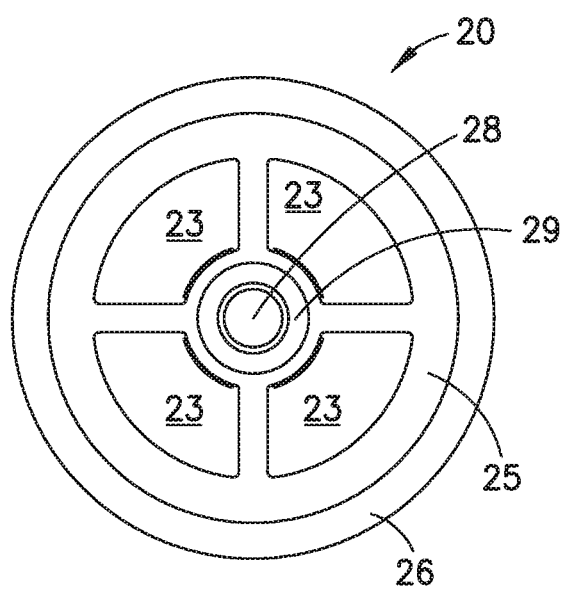
FIG. 5C is a bottom view of the adapter ring shown in FIG. 5A.

FIGS. 5A-5C provide detailed views of adapter ring 20. More specifically, FIG. 5A provides a sectional view of adapter ring 20, FIG. 5B provides a top view of adapter ring 20, and FIG. 5C provides a bottom view of adapter ring 20. As shown in these illustrations, a top surface of adapter ring 20 includes several indentations. An outer indentation 21 including groove 21A forms an internal perimeter on the top surface and is shaped to accommodate placement of o-ring 50. Laterally disposed from indentation 21 is a further indented surface 21B with a generally circular area in the illustrated embodiment. The geometries of these indented areas are largely a matter of design choice. Indented surface 21B tapers downward from an outer edge toward a center of adapter ring 20 where an inner edge of indented surface 21B is defined by a perimeter of cylindrical passage 28. Put another way, indented surface 21B defines a shallow funnel shape. The bottom surface 25 includes an outward taper 29 from cylindrical passage 28. Adapter ring 20 as illustrated also includes four recesses 23 in the bottom surface 25, each shaped as a quarter of a ring shape and separated from one another. As shown in FIG. 5C, recesses 23 are symmetrical about both an x axis and a y axis. Recesses 23 may facilitate a process of manufacturing portions of adapter ring 20 with a substantially uniform thickness. In other embodiments, the number, size, and/or orientation of recesses 23 may be changed. For example, adapter ring 20 could be modified such that it has two, six, or seven recess included in its bottom surface 25.

As best illustrated in FIGS. 6A-6C, sleeve 30 includes a tubular shape so that its body is substantially cylindrical. Sleeve 30 includes two pairs of stress relief slots 34A, 34B extending longitudinally on opposite sides of the body. In between each pair of slots 34A, 34B is a latch 32A, 32B. Latches 32A and 32B taper inward from a wall of sleeve 30 in a proximal direction towards a top rim of the sleeve. Both latches 32A, 32B include a steep angle at their proximal end forming a shelf. Latches 32A and 32B are adapted to correspond to a matching grooves 8A and 8B in bottle 2 to secure sleeve 30 to bottle 2, as shown in FIG. 3. The shape of sleeve 30 maintains securement when engaged to bottle 2 even when the bottle is pressurized by certain microorganisms that by their metabolic process create additional gas in bottle 2. Sleeve 30 is manufactured with flexible properties so that an area inside sleeve 30 can be expanded. One function of these properties is to facilitate disengagement of latches 32A and 32B from grooves 8A and 8B in bottle 2.

Figure 2B:
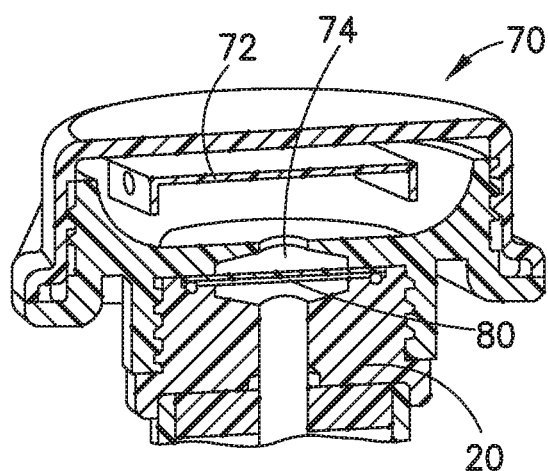
FIG. 2B is a close up partial sectional view of the adapter assembly shown in FIG. 2A with a sensor attached.
Figure 3:
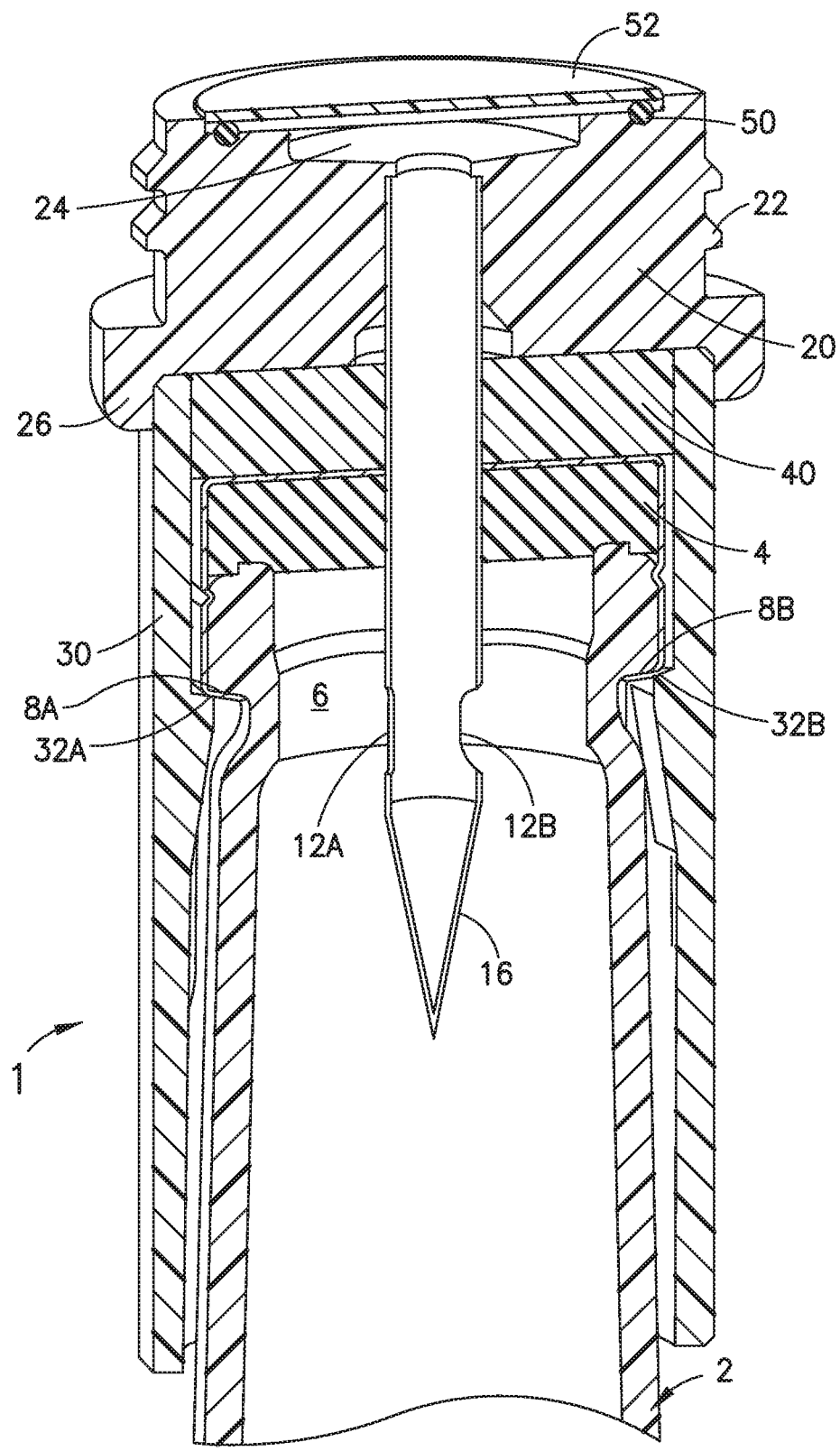
FIG. 3 is a close up sectional view of the adapter assembly.

As shown in FIGS. 2A-3, spacer 40 includes a circular profile with a hole through its centerline, making it a ring like structure. A depth of spacer 40 is cylindrical so that it fits securely within sleeve 30. Spacer 40 may have elastomeric properties or properties allowing it to absorb the tolerances associated with the process of crimping septum 4 onto the finish of bottle 2. This results in a secure fit that prevents the adapter assembly from rattling or moving in a way that would cause leaking at a penetration point. In this way, spacer 40 is a compliant member. In addition, spacer 40 compresses as bottle 2 and adapter 1 are advanced into securement by latches 32A and 32B of sleeve 30 that create a tight fit. In its position surrounding cannula 10, spacer 40 also stabilizes cannula 10. Material properties of the spacer may be the same as those for septum 4, though other materials are contemplated.

As best shown in FIGS. 3 and 5A-5C, o-ring 50 is disposed in indentation 21A on the top surface of adapter ring 20. O-ring 50 includes a circular cross-section and forms a substantially circular perimeter. O-ring 50 may be configured to ensure a gas tight connection with or without the assistance of membrane 52. O-ring 50 can be separate from or integrated with the membrane 52. For example, in some embodiments membrane 52 may have a thin annular ring or rib integrated therewith, which rests on the surface of the adapter ring 20 and surrounds expansion chamber 24, and o-ring 50 may surround the thin annular ring as a separate additional seal. Such an annular ring can be made from polyethylene or other polymers having a low modulus of elasticity.

As best shown in FIGS. 3 and 5A-5C, in an assembled condition, membrane 52 is disposed in indentation 21 of adapter ring 20. A closed space created between membrane 52 and indented surface 21B forms expansion chamber 24. Expansion chamber 24 is designed to define a gas interface from bottle 2 with a large surface area of membrane 52 adjacent to expansion chamber 24. This configuration is selected because gas transmission through membrane 52 is desired, but fluid transmission is prevented. With membrane 52 secured on adapter assembly 1, gas flows into expansion chamber 24 and through membrane 52 and into the sensor 70. Concurrently, liquid ingress into a cavity of an attached sensor assembly (e.g., recess 74 of sensor assembly 70) is prevented. In some embodiments, membrane 52 is an expanded TEFLON or PTFE material embedded with a stainless steel mesh. A membrane with this structure can provide the same benefits as an expanded TEFLON or PTFE membrane in the form of gas permeability without liquid permeability, but can include a much smaller thickness. This, in turn, can reduce a volume needed for the chamber and therefore reduce the potential for contamination of any sample in the bottle.

As shown in FIGS. 1B and 2B, adapter assembly 1 is configured to engage sensor assembly 70. Sensor assembly includes sensor 72. Suitable sensor assemblies are known to those skilled in the art and are not described in detail herein. One example of a suitable sensor chip disposed in a sensor cap is a Sensor Array such as SpecID™ obtained from Specific Technologies. As shown in FIGS. 1B and 2B, sensor assembly 70 also includes threads corresponding to threads 22 of adapter ring 20 for secure engagement between sensor assembly 70 and adapter assembly 1. Sensor assembly 70 also includes recess 74, which proximately mirrors expansion chamber 24 of adapter ring 20. Thus, when adapter assembly 1 is connected to sensor assembly 70, recess 74 and expansion chamber 24 form gas collection chamber 80, which is divided by membrane 52. As shown in FIGS. 1A-6C, the shape of expansion chamber 24 ensures maximum surface area contact with membrane 52 to improve gas delivery to sensor 72 while a volume of expansion chamber 24 is minimized so that during assembly and disassembly, contamination from the external environment is minimized. In some embodiments, sensor assembly 70 may include a raised ring to, for example, seal membrane 52 in place of, or in addition to, o-ring 50. In such embodiments, when the raised ring and a flat surface surrounding expansion chamber 24 of adapter assembly 1 are advanced toward one another into a closed position (i.e., the raised ring is advanced to a position adjacent and corresponding to the flat surface) a gas tight seal may be formed.

The adapter assembly of FIGS. 1A-6C can be varied in many ways. For example, cannula 10 can include three or more ports. As another example, threads 22 on the outside of adapter ring 20 can be substituted with a simple bonded annular ring joint, an ultrasonically welded joint, and/or other joints that would be commonly considered by those practiced in plastic component assembly. As another example, the height and angles of the latches can be tuned and/or otherwise altered to exchange application force for retention force. Application and retention forces may also be tuned by altering the size of the stress relief slots equally disposed about the latches, either in length or edge to edge distance. Furthermore, a person skilled in the art is aware of alternative mechanisms to effectively seal sensor assembly 70 when it is secured to adapter assembly 1.

Some advantages of adapter assembly 1 include provision of a more easily manufactured design over existing adapters by breaking the design into multiple parts for molding and assembly and providing additional features and functionality. It also provides a means of adapting to a host of sensor assembly types and provides for adjustable retention features, such as latches 32A and 32B on sleeve 30. Furthermore, adapter assembly 1 prevents rattling to insure the integrity of the connection between septum 4 and bottle 2 as well as between sleeve 30 and bottle 2.

Yet another advantage is that cannula 10 as described is sized to optimize gas transfer. In particular, cannula 10 is advantageous because a combined cross-sectional area of ports 12A and 12B is equal to or greater than an area formed by an inner diameter of cannula 10 and is sufficiently large to pose relatively low impedance to gas transmission, while at the same time the depth or length taken up by ports 12A and 12B is shorter than the thickness of septum 4. Furthermore, the gas flow impedance of cannula 10 is very small in comparison with the gas flow impedance of membrane 52. This property of the assembly is further evidence of improved gas transfer with the assembly as described. The structure of cannula 10 optimizes gas transfer while also preventing leakage of gas in either direction during installation of adapter assembly 1 onto bottle 2. Another advantage of the assembly described herein is that cannula 10 can provide the above advantages with respect to gas transfer, and do so with a cannula substantially larger in size than those currently known in the art that are designed to minimize gas leakage.

Yet another advantage is that despite the width of expansion chamber 24 relative to a diameter of adapter ring 20, the total internal volume in expansion chamber 24 is minimized so that a maximum amount of gas that could enter bottle 2 through expansion chamber 24 is limited by the small volume of expansion chamber 24. Thus, the amount of atmospheric air that mixes with, for example, a blood culture head space gas when the adapter assembly is secured to the bottle is minimized.

Another aspect of the invention relates to a method of transferring gases using adapter assembly apparatus 1 of FIGS. 1A-6C. The method proceeds as follows. First, membrane 52 is installed in indentation 21 of adapter ring 20 to form expansion chamber 24. Adapter apparatus 1 is then ready for assembly with the sensor and attachment to the bottle.

Sensor assembly 70 is then secured to adapter ring 20. Each of sensor assembly 70 and adapter ring 20 have engagement features that correspond to one another to obtain securement. As shown in FIGS. 1A-6C, these features are threads. When sensor assembly 70 is fully secured to adapter ring 20, cylindrical hole 28 extends in an upward direction directly into gas collection chamber 80. In this configuration, membrane 52 divides the pathway to sensor 72 from bottle 2. As described above, gas is transmitted from within bottle 2, through membrane 52 and then toward sensor 72 via sensor assembly 70. Membrane 52 prevents fluids from passing therethrough at all times during this process. Further, o-ring 50 at a perimeter of membrane maintains a gas seal preventing any external gases or other matter from entering any volume of bottle 2, sensor assembly 70, or pathways in between. Of course, with other sensors not shown or described, it is contemplated that a particular path of travel for gases within a sensor assembly can vary.

Next, adapter assembly 1 is placed over bottle 2, as shown in FIGS. 1A-3. During this process, as cannula 10 penetrates septum 4 and advances through it minimal interaction occurs between the external environment and the contents of bottle 2 since ports 12A and 12B of cannula are shorter in depth than a thickness of septum 4. Accordingly, ports 12A and 12B are never simultaneously exposed to air above and below the septum and therefore leakage is prevented in either direction during insertion. In addition, cannula 10 penetrates septum with forces sufficiently low to prevent the septum from being dislodged from a crimp ring holding it in place. As mentioned above, in one example, these objects are achieved with the use of BD's Whiteacre point cannula. Low force insertion is also possible because of the manner in which latches 32A and 32B of sleeve 30 are constructed. Adapter assembly 1 is advanced onto bottle 2 until latches 32A and 32B on sleeve 30 snap into corresponding grooves 8A and 8B on bottle 2.

Upon removal of adapter assembly from bottle 2, pierced septum 4 of bottle 2 closes and forms a gas tight seal. Thereafter, septum 4 will continue to function properly, preventing contaminants from entering bottle 2 and preserving whatever pressure, negative or positive, in bottle 2. Removal of adapter assembly 1 is simplified through the manner in which latches 32A, 32B are configured. Removal may be necessary in some instances, for example, to subculture bottle 2.

As shown in FIG. 7, yet another aspect of the invention relates to a method of assembly of the constituent parts of adapter assembly 1. In a first step, cannula 10 is inserted into adapter ring 20 from the bottom side of adapter ring 20. Prior to insertion, cannula 10 is coated or otherwise prepared with an adhesive (not shown) so that following insertion, cannula is secured within adapter ring 20. In one example, an adhesive placed on cannula 10 is a UV cured epoxy. In a second step, spacer 40 is slid over cannula 10 from below adapter ring 20. Spacer 40 includes a central opening which cannula 10 passes through. In a third step, the elements so far combined are placed over sleeve 30. Adapter ring 20 secures to sleeve 30 through connection arms 26 engaging an outside surface of sleeve 30. In a fourth step, o-ring 50 is placed into indentation 21A of adapter ring 20.

Figure 9:
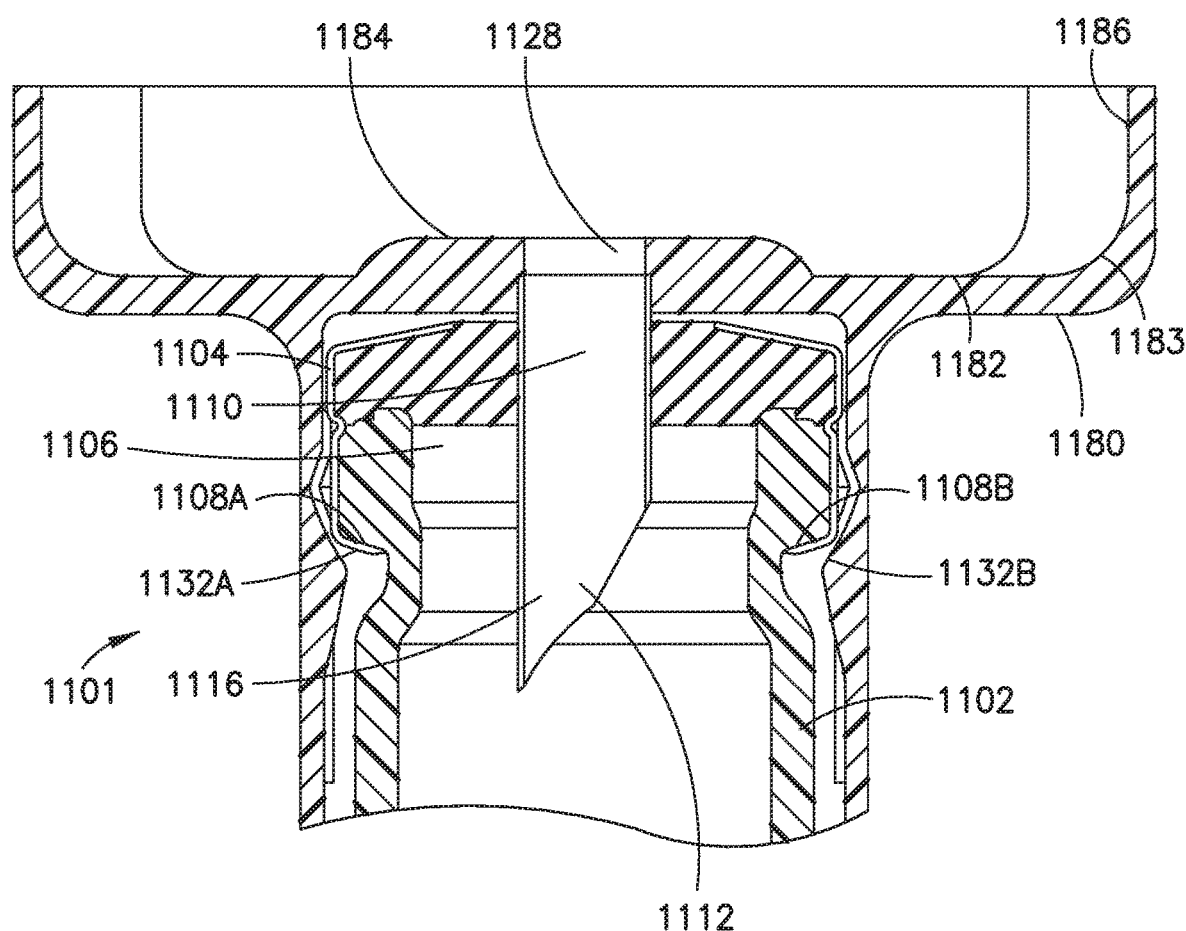
FIG. 9 is a partial sectional view of the adapter assembly of FIG. 8A.

FIGS. 8A-9 illustrate an adapter assembly that is a cannula combined with a single monolithic part having a cylindrical lower portion for disposal over a bottle and an upper tray portion flaring outward from the lower portion. An opening exists in a longitudinal center of the bottom of the tray sized for placement of a cannula therethrough. As shown in FIGS. 8A-9, adapter assembly 1101 includes cannula 1112 and a single injection molded part with a lower sleeve portion 1130 and upper tray portion 1180. As best shown in FIG. 9, cannula 1110 includes a distal portion 1116 constituting a needle bevel. An opening of the bevel is a single port 1112. Cannula 1110 is configured to be disposed within a cylindrical opening 1128 in tray portion 1180 and in fluid communication therewith, and is secured in place with an adhesive.

Sleeve portion 1130 of adapter assembly 1101 is tubular in section and includes an interior diameter sized to conform to fit over a cap portion of a bottle, such as the cap of a BACTEC™ bottle. Sleeve portion 1130 includes four pairs of slots 1134A and 1134B extending vertically on a surface of sleeve portion 1130. Each pair of slots is approximately equidistant from an adjacent pair so that about ninety degrees of sleeve surface measured from a center of the sleeve separates each pair.

On an interior surface of sleeve portion 1130 are two latches 1132A, 1132B positioned opposite each other as shown in FIG. 9. Each latch 1132A, 1132B forms a shelf inside sleeve portion 1130. From an inner wall of sleeve portion 1130, an upper surface of latch 1132A, 1132B extends at a steep angle from the inner wall. This forms the shelf of the latch 1132A, 1132B. The shelf portion extends into indentations in the surface of the bottle 1102, securing the sleeve 1101 onto the bottle 1102. One skilled in the art is aware of other mechanisms and arrangements by which a sleeve may be secured to a bottle. From an edge of the shelf furthest from the inner wall of sleeve portion 1130, the latch tapers downward away from the shelf back towards the inner wall of the sleeve portion 1130. As shown in the example illustrated in FIG. 9, the lower tapered portion of latch tapers at different angles with respect to the inner wall at different locations on the latch.

Extending from sleeve portion 1130 in a proximal direction away from a distal end 1138 of sleeve portion 1130 is tray portion 1180. Tray portion 1180 includes cylindrical opening 1128 for disposing cannula 1110 therethrough and is bounded on all sides by wall 1186, which forms a four sided perimeter. Cylindrical hole 1128 is located at a center of raised portion 1184, at a longitudinal center of adapter assembly 1101. Wall 1186 includes a substantially constant thickness through its upper portion, and includes curved surfaces 1183 towards a base 1182 of tray portion 1180. Base 1182 defines a tray surface within walls 1186, and at its center, includes a raised portion 1184.

Much like assembly adapter 1 of FIGS. 1A-6C, adapter assembly 1101 advantageously includes a snap on engagement feature, which can be used on plethora of bottle configurations without the need for changing the design of assembly 1101. Thus, time and expense are saved because there is no need to prepare multiple mold sizes and/or types for the assembly. Furthermore, much like assembly adapter 1 of FIGS. 1A-6C, securement and operation of adapter assembly 1101 can be accomplished without having to replace septum 1104 with another element. Instead, cannula 1110 punctures septum 1104, but when removed, septum 1104 expands so that an air tight seal is formed by septum 1104 to prevent any gases from escaping bottle 1102 when adapter assembly 1101 is detached from the bottle 1102. Still further, much like assembly adapter 1 of FIGS. 1A-6C, the integration of latches 1134A, 1134B with sleeve portion 1130 eliminates the need for additional snapping mechanisms for engagement between sleeve portion 1130 and the bottle 1102.

Another embodiment involves a method of installation to secure adapter assembly 1101 of FIGS. 8A-9 to bottle 1102. Initially, cannula 1110 is secured within opening 1128 of adapter assembly 1101 via an adhesive (not shown). Because adapter assembly 1101 is monolithic, adapter assembly 1101 is then ready for securement to bottle 1102. FIG. 9 illustrates a close up section of adapter assembly 1101 and bottle 1102 and shows grooves 1108A, 1108B extending around an outer perimeter of bottle 1102. Adapter assembly 1101 is advanced over the cap of bottle 1102 by placing walls of sleeve portion 1130 over an external surface of bottle 1102. Latches 1132A, 1132B on sleeve portion 1130 snap onto grooves 1108A, 1108B of bottle 1102. During the above advancement, cannula 1110 pierces septum 1104 of bottle 1102 and enters a headspace 1106 of bottle 1102. This creates a passage for gases to flow from within bottle 1102 into tray portion 1180.

In yet another method, gases are transferred using adapter assembly 1101. When adapter assembly 1101 is engaged with bottle 1102 as described above, gases flow from bottle 1102 through cannula 1110 via cannula port 1112 and into tray portion 1180 of adapter assembly 1101. A sensor cap assembly (not shown) disposed on tray portion 1180 then reads and/or measures gas parameters flowing into the tray portion 1180 from the bottle 1102 via cannula 1110. A wide variety of sensors can be used in conjunction with this method. Much like sensor assembly 70 of FIGS. 1A-6C, the sensor cap assembly seals the top of tray portion 1180 from the environment, thus ensuring that contaminants do not enter tray portion 1180 and that gases do not escape from bottle 1102.

Figure 10:
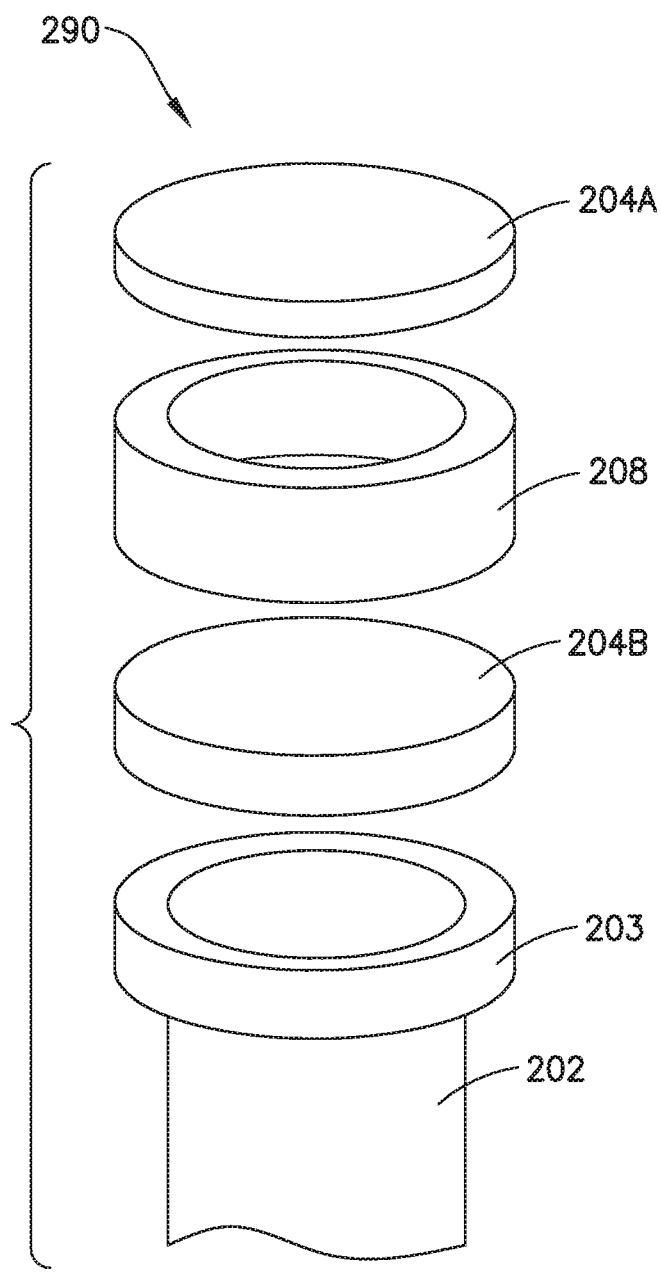
FIG. 10 is a profile view of yet another embodiment of an adapter assembly.

FIG. 10 illustrates an apparatus for preventing venting of gases from a bottle during insertion of a bevel-cut cannula into the bottle. As shown in FIG. 10, apparatus 290 includes septum 204A, over rim 208, over another septum 204B, placed in that order, onto lip 203 of bottle 202. A cap (not shown) for bottle 202 must be at least as deep as a combined depth of septum 204A, rim 208 and septum 204B. Further, a bevel depth of a cannula must be less than or equal to a thickness of rim 208. This embodiment is advantageous in that when all layers are in place, the apparatus improves or eliminates possible venting during insertion of a bevel-cut cannula into a bottle. In some embodiments, apparatus 290 may replace, or be disposed beneath, a spacer in an adapter assembly similar to the one described with reference to FIGS. 1A-6C.

FIGS. 11A and 11B illustrate a dual-function adapter assembly. As shown in FIGS. 11A and 11B, dual-function adaptor 140 includes outer blood collection adapter 110, which includes adapter 101, needle 102, and outer adaptor housing 103. In some embodiments, outer blood collection adapter 110 may be implemented using BD's Vacutainer® One Use Holder. Furthermore, in some embodiments, adapter 101 may be implemented using BD's Vacutainer® Multiple Sample Luer Adapter.

Dual-function adaptor 140 also includes inner sensor array adaptor 130, which includes septum 104, sensor array 105, outer needle 106, snap-fit lock 107, inner adaptor housing 108, seal 109, and gas collection chamber 150. As shown in FIGS. 11A and 11B, inner adaptor housing 108 which has a smaller diameter than outer adaptor housing 103 so that inner sensor array adaptor 130 can be loosely fitted into outer blood collection adapter 110. Outer needle 106 and gas collection chamber 150 provide Inner sensor array adaptor 130 with an open channel for sensor array 105 to receive a volatile organic compound ("VOC") produced by microbial growth in a collection vessel on which inner adaptor 130 is placed. As shown in FIGS. 11A and 11B, inner needle 102 has a shorter and smaller diameter gauge in size than that of the outer needle 106.

Dual-function adaptor 140 is assembled by inserting inner sensor array adaptor 130 into outer blood collection adapter 110 via the puncture by needle 102 through septum 104. Dual-function adaptor 140 is preferably packaged under appropriate biologically and chemically inert gas-filled packaging or similar with proper sterilization process for clinical and hospital usage. In some embodiments, the design of dual-function adaptor 140 allows a health care worker to insert dual-function adaptor 140 into a blood culture bottle to transfer a blood sample into a collection vessel in a conventional manner. After completion the blood collection process, outer adapter 110 is removed from the blood culture bottle while the inner sensor array adaptor 130 is retained on the blood culture bottle via snap-fit lock 107. Thus, sensor array 105 remains in gas communication with the blood culture bottle on which inner sensor array adaptor 130 remains secured.

Figure 12C:
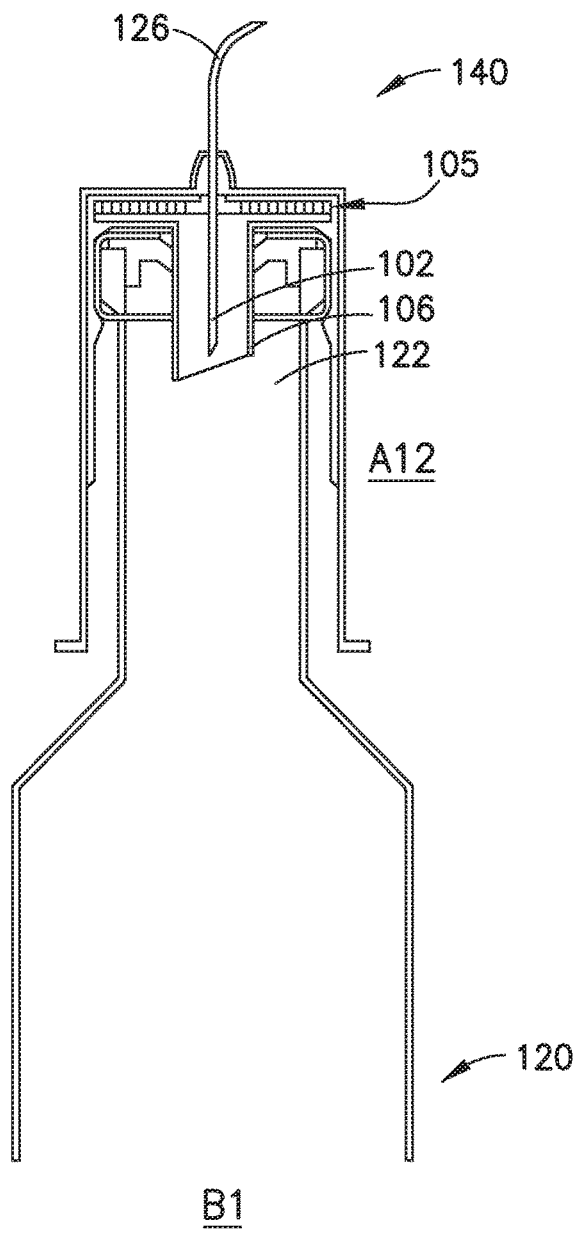
Figure 12D:
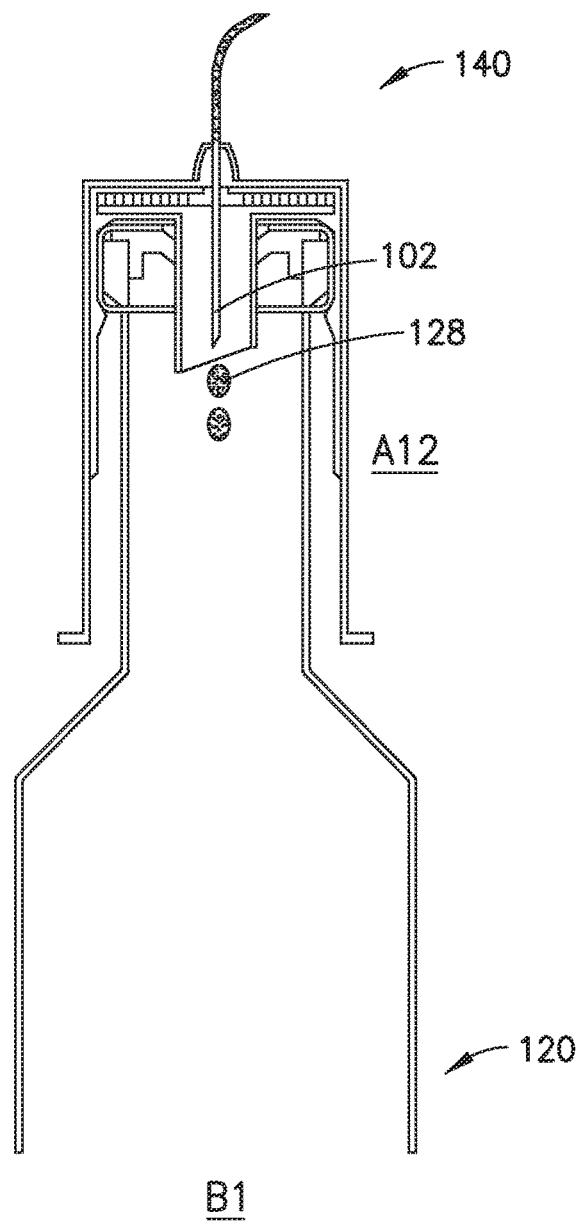

The operation of dual-function adaptor 140 is illustrated in FIGS. 12A-12F. In FIG. 12A, dual-function adaptor 140 is placed over bottle 120 with septum 124. In FIG. 12B, dual-function adaptor 140 is advanced onto bottle 120 such that outer needle 106 contacts septum 124. Furthermore, inner needle 102 is connected to tubing 126 for sample collection. In FIG. 12C, outer needle 106 pierces septum 124 and outer needle 106 allows gaseous communication between headspace 122 of bottle 120 and sensor array 105. Furthermore, during this process, seal 109 is broken. Seal 109 may include an easily punctured material, such an aluminum foil or a thin silicone membrane. Moreover, seal 109 may be sterilized prior to use. As shown in FIG. 12D, sample 128 is collected in bottle 120 through inner needle 102 and tubing 126. As shown in FIG. 12E, once sample collection is complete, outer adaptor housing 103 is removed from the bottle 120, but inner adaptor housing 108 remains secured thereon. As shown in FIG. 12F, Bottle 120 remains sealed after inner needle 102 is removed from septum 104.

Figure 13A:
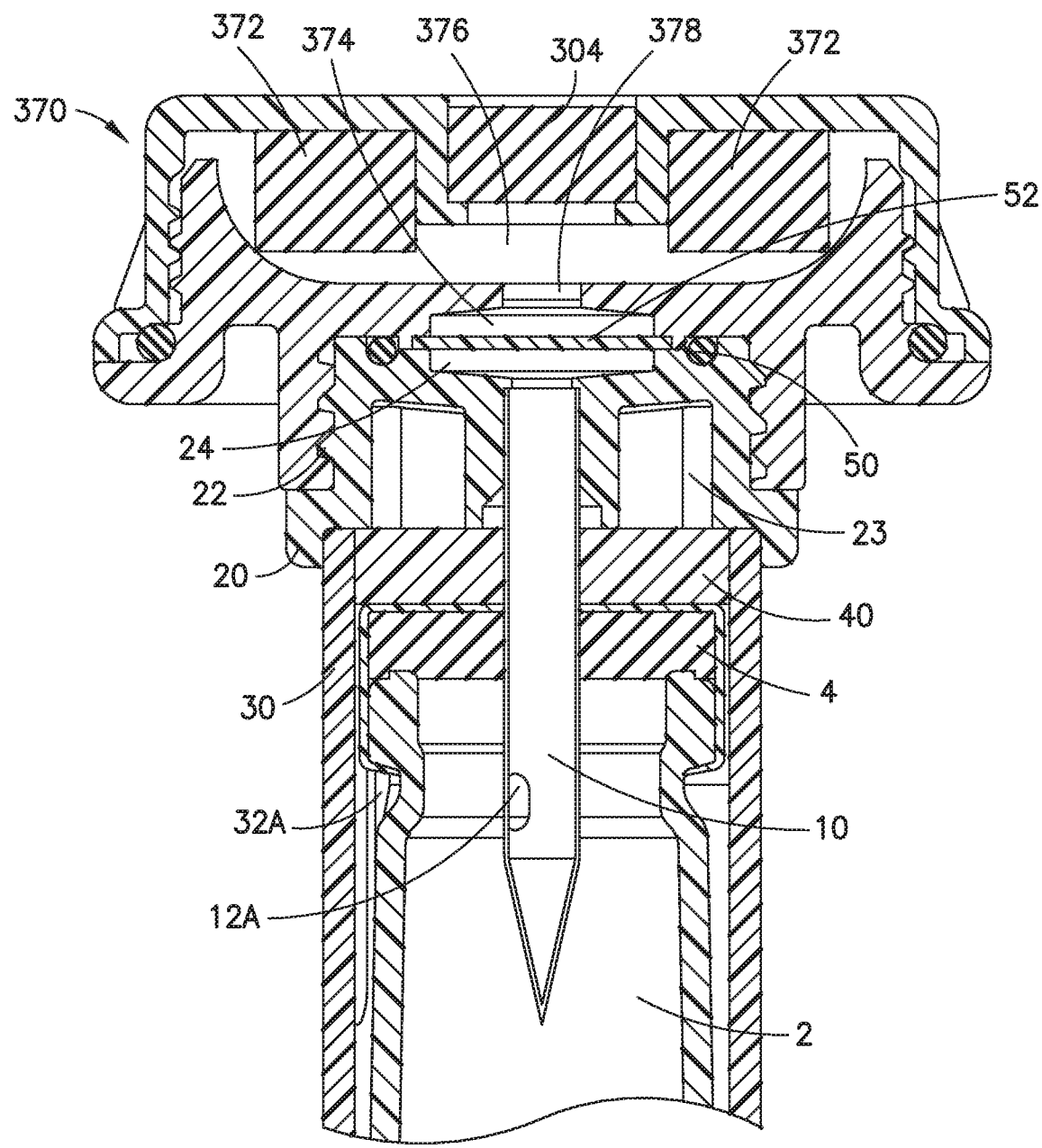
FIGS. 13A and 13B are sectional views of the adapter assembly of FIGS. 1A through 6C with a different sensor assembly attached thereto.
Figure 13B:
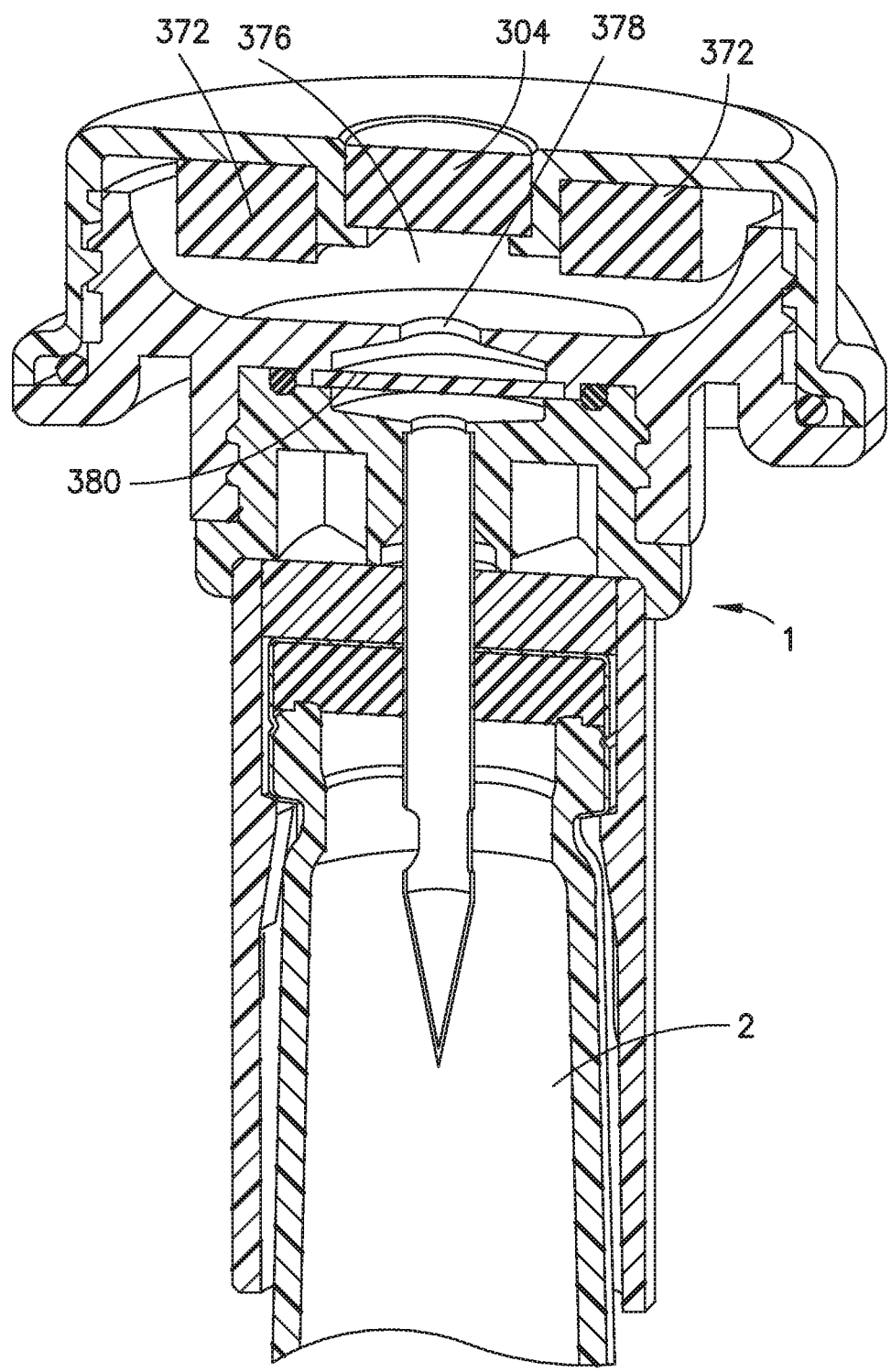
Figure 13C:
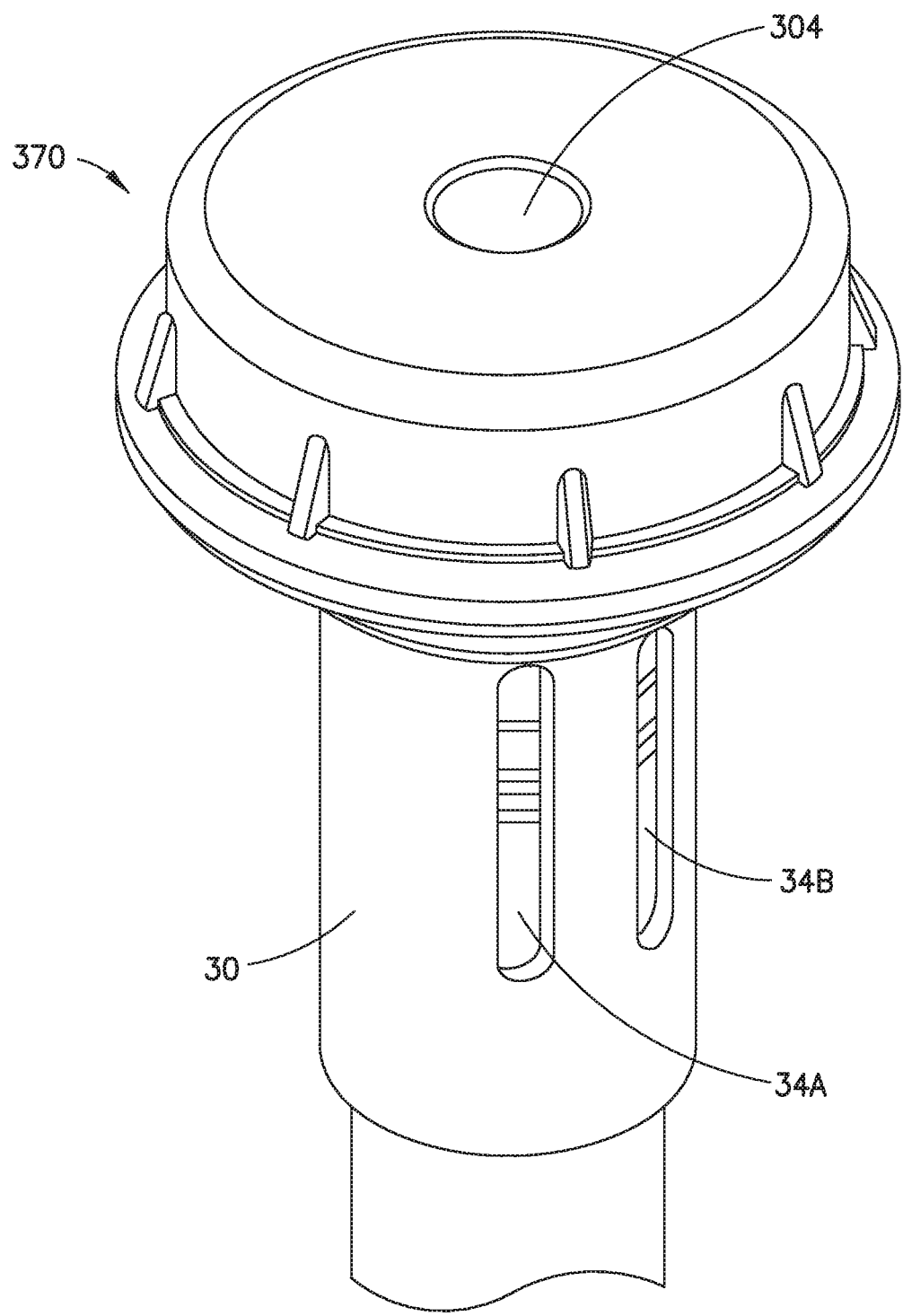
FIG. 13C is an external view of the adapter assembly and the sensor assembly of FIGS. 13A and 13B.

The embodiment of FIGS. 1A-6C can be readily adapted to include some of the features described above with reference to FIGS. 11A-12C. For example, as shown in FIGS. 13A-13C, a different sensor assembly (e.g., sensor assembly 370) can be attached to adapter assembly 1 of FIGS. 1A-6C. As shown in FIGS. 13A-13C, sensor assembly 370 includes sensor 372, recess 374, sensor chamber 376, and conduit 378. When adapter assembly 1 is connected to sensor assembly 370, recess 374 and expansion chamber 24 form gas collection chamber 380. As shown in FIGS. 13A-13C, a large surface area of membrane 52 is exposed inside gas collection chamber 380 to promote the flow of gas from the headspace of bottle 2 toward sensor chamber 376. In contrast to sensor assembly 70 of FIGS. 1A-6C, sensor assembly 370 also includes septum 304. Much like septum 104 of FIGS. 11A-12C, septum 304 may receive a needle for accessing the gases in sensor chamber 376. Furthermore, in contrast to sensor 72 of FIGS. 1A-6C, sensor 372 has a circular shape with a hole in the middle for septum 304. Sensor 72 may be constructed with a rigid material and be configured to fit snuggly around septum 304.

In some embodiments, sensor 372 may be replaced with another sensor having a different size and shape. Furthermore, in some embodiments, sensor chamber 376 may be configured to minimize the space surrounding sensor 372 so as to minimize the degree to which gases from the headspace of bottle 2 are diluted. In some embodiments membrane 52 may be pierceable or eliminated from adapter ring 20 entirely. In such embodiments, a needle having a shorter and smaller diameter gauge in size than that of cannula 10 (e.g., needle 102 of FIGS. 11A-12C) can be used to withdraw or dispense a sample into bottle 2. For example, a narrow needle having such dimensions may be inserted into bottle 2 through septum 304 and cannula 10. Furthermore, much like inner sensor array adaptor 130 of FIGS. 11A-12C, adapter assembly 1 and sensor assembly 370, collectively, may be loosely fitted into an outer blood collection adapter, such as BD's Vacutainer® One Use Holder.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adapter assembly comprising:
a sleeve configured to engage a collection vessel;
a cannula configured to penetrate a septum of the collection vessel; and
a sensor assembly interface configured to engage a sensor assembly comprising a gas sensor sensitive to changes in a composition of gases in a headspace of the collection vessel, wherein the sensor assembly interface is connected to the sleeve and the cannula,
wherein the adapter assembly is configured such that when (i) the sleeve is engaged with a collection vessel and (ii) the sensor assembly interface is engaged with the sensor assembly:
(a) the sensor assembly interface and the cannula provide a flow pathway for delivering gases from the headspace of the collection vessel to the gas sensor of the sensor assembly; and
(b) the sensor assembly interface defines a first portion of an expansion chamber for collecting the gases in the flow pathway from the headspace of the collection vessel, wherein the sensor assembly defines a second portion of the expansion chamber wherein a membrane divides the first portion of the expansion chamber from the second portion of the expansion chamber wherein the membrane allows gases in the flow pathway to flow toward the gas sensor and prevents liquid in the collection vessel from contacting the gas sensor.

2. The adapter assembly of claim 1, wherein the adapter assembly is configured to form a closed system when (i) the sleeve is engaged with the collection vessel and (ii) the sensor assembly interface is engaged with the sensor assembly.

3. The adapter assembly of claim 1, wherein the membrane is interposed between the portion of the sensor assembly interface and the portion of the sensor assembly.

4. The adapter assembly of claim 3, wherein the membrane is a polytetrafluoroethylene material embedded with a stainless steel mesh.

5. The adapter assembly of claim 1, wherein the sleeve includes two opposing latches for engaging the collection vessel, and wherein both latches taper inward from a wall of the sleeve in a proximal direction towards a top rim of the sleeve.

6. The adapter assembly of claim 5, wherein the sleeve includes two pairs of stress relief slots extending longitudinally on opposite sides of the sleeve, and wherein one of the two opposing latches is positioned between one of the two pairs of stress relief slots, and wherein the other opposing latch is positioned between the other pair of stress relief slots.

7. The adapter assembly of claim 1, wherein the cannula includes a first portion that is substantially cylindrical and a second portion that is tapered to a point at one end, and wherein the first portion includes at least one port.

8. The adapter assembly of claim 7, wherein the cannula comprises two ports located approximately opposite each other on the cannula.

9. The adapter assembly of claim 1, wherein the sensor assembly interface is an adapter ring having a substantially cylindrical shape.

10. The adapter assembly of claim 9, wherein the adapter ring is threaded for engaging the sensor assembly and wherein the sleeve includes a substantially cylindrical body, and wherein the adapter ring seals one end of the body of the sleeve, and wherein the cannula is disposed in a central opening of the adapter ring and extends therethrough.

11. The adapter assembly of claim 10 further comprising:
a circular spacer disposed on a bottom surface of the adapter ring around the cannula; and
an o-ring disposed on a top surface of the adapter ring, wherein the o-ring forms a gas tight seal when the sensor assembly interface is engaged with the sensor assembly.

12. The adapter assembly of claim 1, wherein the sleeve and the sensor assembly interface are monolithically integrated as a single component or are separate components attached together.

13. The adapter assembly of claim 1 further comprising:
the sensor assembly, wherein (i) the sensor assembly is welded to the sensor assembly interface, (ii) attached to the sensor assembly interface with an adhesive, or (iii)

the sensor assembly and the sensor assembly interface are monolithically integrated as a single component.

14. The adapter assembly of claim 1 further comprising: the sensor assembly; and
a septum disposed on a top surface of the sensor assembly such that a needle having a smaller diameter than the cannula is adapted to puncture the septum disposed on the top of the sensor assembly and enter the collection vessel through the cannula and the chamber.

15. The adapter assembly of claim 1 further comprising: the sensor assembly, wherein the sensor assembly includes a sensor chamber with the sensor disposed therein; and
a septum disposed on a top surface of the sensor assembly such that a needle is adapted to puncture the septum and provide access to gases inside the sensor chamber.

16. A method of measuring a composition of gases in a headspace of a collection vessel, the method comprising:
providing a sensor assembly defining a first portion of an expansion chamber with a sensor assembly interface of an adapter assembly that defines a second portion of an expansion chamber;
wherein a membrane has been installed between the sensor assembly and the sensor assembly interface prior to engaging the sensor assembly and the sensor assembly interface, wherein the membrane is configured to:
allow gases in a flow pathway to flow toward the gas sensor; and
prevent liquid in the collection vessel from contacting the gas sensor;
engaging the sensor assembly and the sensor assembly interface;
piercing a septum of a collection vessel with a cannula of the adapter assembly;
advancing a sleeve of the adapter assembly along a portion of the collection vessel until the adapter assembly is engaged with the collection vessel; and
measuring a composition of gases contacting a gas sensor of the sensor assembly, wherein the sensor is sensitive to changes in a composition of the gases, and wherein the gases flow from a headspace of the collection vessel and towards the gas sensor through a flow pathway comprising the cannula and a chamber, a first portion of which is defined by the sensor assembly interface and a second portion of which is defined in the sensor assembly.

17. The method of claim 16, wherein the steps of engaging, piercing, and advancing form a closed system comprising the sensor assembly, the adapter assembly, and the collection vessel.

18. The method of claim 16, wherein the sleeve includes two opposing latches for engaging the collection vessel, and wherein both latches taper inward from a wall of the sleeve in a proximal direction towards a top rim of the sleeve and wherein the sleeve includes two pairs of stress relief slots extending longitudinally on opposite sides of the sleeve, and wherein one of the two opposing latches is positioned between one of the two pairs of stress relief slots, and wherein the other opposing latch is positioned between the other pair of stress relief slots.

19. The method of claim 16, wherein the adapter assembly comprises an adaptor ring having a plurality of circumferentially distributed threads for engaging the sensor assembly and wherein the sleeve includes a substantially cylindrical body, and wherein the adapter ring seals one end of the body of the sleeve, and wherein the cannula is disposed in a central opening of the adapter ring and extends therethrough.

20. The method of claim 19 wherein a circular spacer is installed on a bottom surface of the adapter ring around the cannula; and
an o-ring is installed on a top surface of the adapter ring, wherein the o-ring forms a gas tight seal when the sensor assembly interface is engaged with the sensor assembly.

21. The method of claim 16, wherein (i) the sensor assembly is welded to the sensor assembly interface, (ii) attached to the sensor assembly interface with an adhesive, or (iii) the sensor assembly and the sensor assembly interface are monolithically integrated as a single component.

22. A sensor assembly comprising:
a sleeve configured to engage a collection vessel;
a cannula configured to penetrate a septum of the collection vessel;
a sensor assembly interface engaged with a sensor assembly with a gas sensor sensitive to changes in a composition of gases in a headspace of the collection vessel;
a septum disposed on a top surface of the sensor assembly such that a needle having a smaller diameter than the cannula is adapted to puncture the septum disposed on the top of the sensor assembly and enter the collection vessel through the cannula and a chamber in which the sensor assembly is placed;
a first housing comprising the sleeve, the cannula, the sensor assembly interface, and the sensor assembly; and
a second housing comprising a needle having a smaller diameter than the cannula,
wherein the first housing is loosely fitted inside the second housing;
wherein when (i) the sleeve is engaged with a collection vessel and (ii) the sensor assembly interface is engaged with the sensor assembly:
(a) the sensor assembly interface and the cannula provide a flow pathway for delivering gases from the headspace of the collection vessel to the sensor of the sensor assembly; and
(b) the sensor assembly interface defines the chamber for collecting the gases in the flow pathway from the headspace of the collection vessel.

23. The sensor assembly of claim 22, wherein the needle pierces a seal on the cannula as the first housing is loosely fitted inside the second housing and wherein the needle has a channel that is in fluid communication with the collection vessel when (i) the sleeve is engaged with a collection vessel, (ii) the sensor assembly interface is engaged with the sensor assembly, and (iii) the first housing is loosely fitted inside the second housing.

24. A method of measuring a composition of gases in a headspace of a collection vessel, the method comprising:
providing an inner sensor array adapter comprising a housing, a septum, a sensor array disposed in a gas collection chamber, an inner sensor array adapter needle forming an open channel with the gas collection chamber wherein the septum is formed in axial arrangement with the inner sensor array adapter needle;
providing an outer adapter comprising a housing wherein a is disposed in the housing of the outer adapter and wherein the inner sensor array adapter is received in the outer adapter;

assembling the inner sensor array adapter to the outer adapter such that the needle in the outer adapter pierces the septum of the inner sensor array adapter and the needle of the adapter is received into the inner sensor array adapter needle;

advancing the outer adapter with the inner sensor array adapter received therein along a portion of the collection vessel until the outer adapter is engaged with the collection vessel, thereby piercing the septum of the collection vessel with the inner sensor array adapter needle; and measuring the composition of gases contacting the sensor array, wherein the sensor array is capable of detecting the composition of the gases, and wherein the gases flow from the headspace of the collection vessel and towards the sensor array through a flow pathway comprising the open channel.

\* \* \* \* \*